United States Patent
Baker et al.

(10) Patent No.: US 6,855,277 B2
(45) Date of Patent: Feb. 15, 2005

(54) METHOD AND APPARATUS FOR LIPOSOME PRODUCTION

(75) Inventors: Martin T. Baker, Petaluma, CA (US); William A. Heriot, Las Vegas, NV (US)

(73) Assignee: Optime Therapeutics, Inc., Petaluma, CA (US)

( * ) Notice: Subject to any disclaimer, the term of this patent is extended or adjusted under 35 U.S.C. 154(b) by 261 days.

(21) Appl. No.: 10/298,143

(22) Filed: Nov. 15, 2002

(65) Prior Publication Data

US 2003/0124033 A1 Jul. 3, 2003

Related U.S. Application Data

(63) Continuation of application No. 09/439,619, filed on Nov. 12, 1999, now Pat. No. 6,534,018.
(60) Provisional application No. 60/108,355, filed on Nov. 13, 1998.

(51) Int. Cl.[7] .............................. B01J 13/02; A61K 9/52
(52) U.S. Cl. ........................ 264/4.3; 422/128; 424/450; 425/5; 428/402.2
(58) Field of Search .................. 264/4.3, 4.1; 424/450; 428/402.2; 425/5; 422/128

(56) References Cited

U.S. PATENT DOCUMENTS

| | | |
|---|---|---|
| 3,645,911 A | 2/1972 | Van Besauw et al. |
| 3,804,776 A | 4/1974 | Yazawa et al. |
| 4,016,100 A | 4/1977 | Suzuki et al. |
| 4,089,801 A | 5/1978 | Schneider |
| 4,106,115 A | 8/1978 | Takahashi et al. |
| 4,235,871 A | 11/1980 | Papahadjopoulos et al. |
| 4,438,052 A | 3/1984 | Weder et al. |
| 4,452,747 A | 6/1984 | Gersonde et al. |
| 4,485,054 A | 11/1984 | Mezei et al. |
| 4,532,089 A | 7/1985 | MacDonald |
| 4,551,288 A | 11/1985 | Kelly |
| 4,687,661 A | 8/1987 | Kikuchi et al. |
| 4,737,276 A | 4/1988 | Adamich et al. |
| 4,752,425 A | 6/1988 | Martin et al. |
| 4,761,288 A | 8/1988 | Mezei |
| 4,781,871 A | 11/1988 | West, III et al. |
| 4,853,228 A | 8/1989 | Wallach et al. |
| 4,855,090 A | 8/1989 | Wallach |
| 4,895,452 A | 1/1990 | Yiournas et al. |
| 4,935,171 A | 6/1990 | Bracken |
| 5,013,497 A | 5/1991 | Yiournas et al. |
| 5,271,881 A | 12/1993 | Redding, Jr. |
| 5,453,447 A | 9/1995 | End et al. |
| 5,474,848 A | 12/1995 | Wallach |
| 5,554,382 A | 9/1996 | Castor |
| 5,558,820 A | 9/1996 | Nagano et al. |
| 5,628,936 A | 5/1997 | Wallach |
| 5,653,996 A | 8/1997 | Hsu |
| 5,700,482 A | 12/1997 | Frederiksen et al. |

OTHER PUBLICATIONS

Bangham et al., "Diffusion of Univalent Ions Across the Lamellae of Swollen Phospholipids," *J. Biol. Mol.*, 13:238–252, 1965.

Barenholzt et al., "A New Method for Preparation of Phospholipid Vesicles (Liposomes)—*French Press*," FEBS Letters, 99(1):210–214, 1979.

Batzri et al., "Single Bilayer Liposomes Prepared without Sonication," *Biochimica et Biophysica Acta*, 298:1015–1019, 1973.

(List continued on next page.)

*Primary Examiner*—Krisanne Jastrzab
(74) *Attorney, Agent, or Firm*—Townsend and Townsend and Crew LLP

(57) ABSTRACT

A new method of producing liposomes is described using an in-line mixing system. The liposomes produced by this method find utility in numerous therapeutic applications.

24 Claims, 9 Drawing Sheets

OTHER PUBLICATIONS

Callow et al., "Thermodynamic Modeling and Cryomicroscopy of Cell–Size, Unilamellar, and Paucilamellar Liposomes," *Cryobiology,* 2:251–267, 1985.

Huang, "Studies on Phosphatidylcholine Vesicles. Formation and Physical Characteristics," *Biochemistry,* 8(1):344–352, 1969.

Deamer et al., "Large Volume Liposomes by an Ether Vaporization Method," *Biochimica et Biophysica Acta,* 443:629–634, 1976.

Kim et al., "Preparation of Multivesicular Llposomes," *Biochimica et Biophysica Acta,* 728:339–348, 1983.

Papahadjopoulous et al., "Phospholipid Model Membranes. I. Structural Characteristics of Hydrated Liquid Crystals," *Biochimica et Biophysica Acta,* 135:624–638, 1967.

Weder et al., Liposome Technology. vol. I Preparation of Liposomes, Ed. Gragoriadis, Chap. 7, pp. 79–107, CRC Press, Inc., FL, 1984.

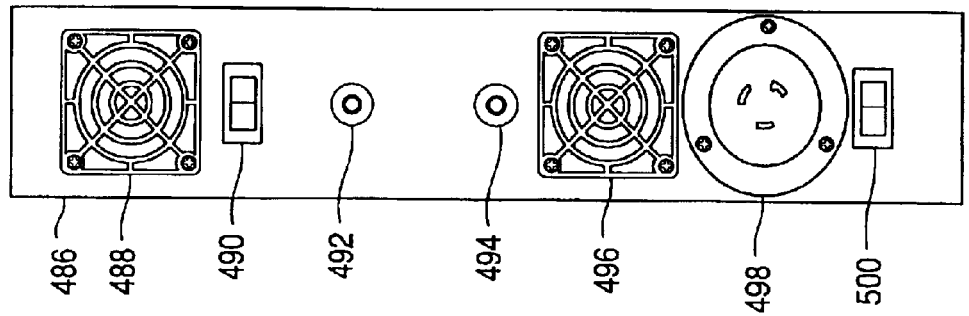
FIG. 20
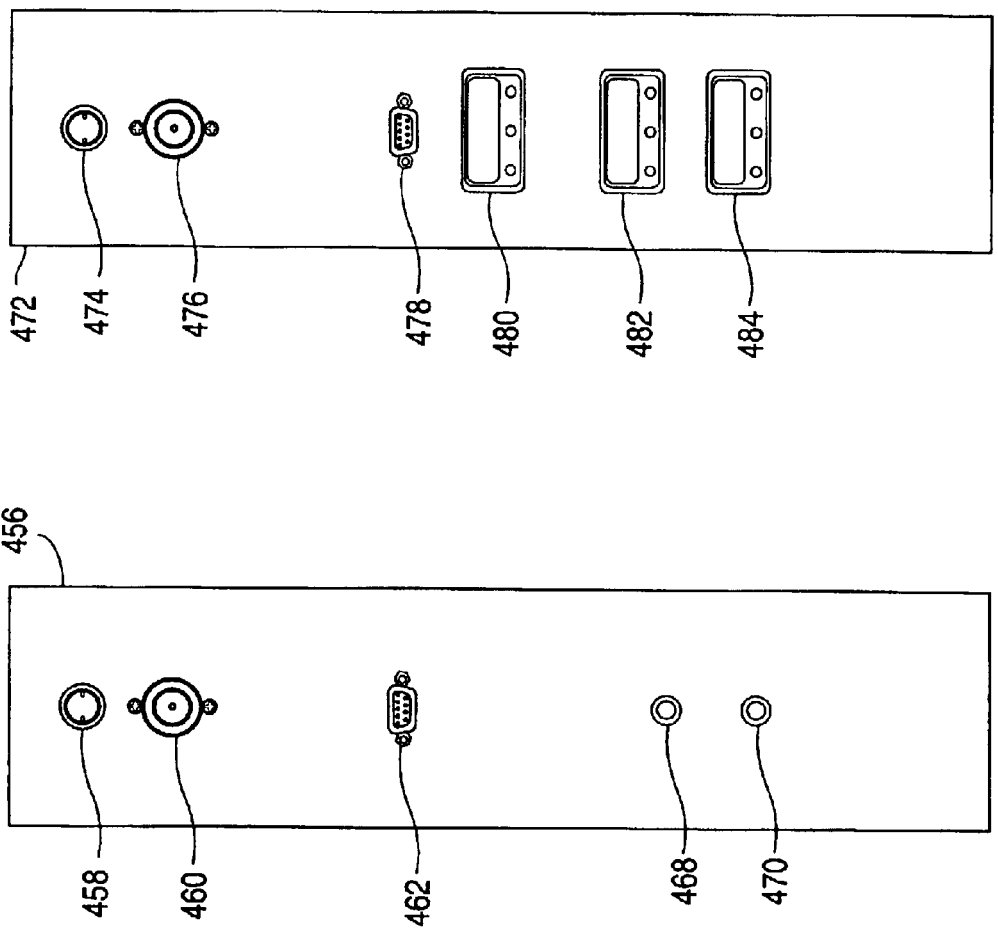
FIG. 19
FIG. 18

METHOD AND APPARATUS FOR LIPOSOME PRODUCTION

CROSS REFERENCE TO RELATED APPLICATION

This application is a continuation of 09/439,619 filed on Nov. 12, 1999 now U.S. Pat. No. 6,534,018 and claims the benefit of U.S. Provisional Application No. 60/108,355, filed on Nov. 13, 1998.

BACKGROUND OF THE INVENTION

1. Technical Field

The present invention relates to a formulation for the delivery of a variety of beneficial and/or therapeutic compounds by encapsulation within liposomes, and a machine of unique design for the controlled production of same. Specifically the invention relates to a precisely controlled metering system for the mixing of the two or more components of the liposomal preparations so that the various factors affecting the consistency, reproducibility and efficacy of the product may be monitored and controlled. The present invention also relates to a method and apparatus for the production of liposomal suspensions, emulsions, ointments and creams.

2. Background

Liposomes are lipid vesicles made of membrane-like lipid bilayers separated by aqueous layers. Liposomes have been widely used to encapsulate biologically active agents for use as drug carriers since water- or lipid-soluble substances may be entrapped within the aqueous layers or within the bilayers themselves. There are numerous variables that can be adjusted to optimize this drug delivery system. These include, the number of lipid layers, size, surface charge, lipid composition and the methods of preparation.

Liposomes have been utilized in numerous pharmaceutical applications, including injectable, inhalation, oral and topical formulations, and provide advantages such as controlled or sustained release, enhanced drug delivery, and reduced systemic side effects as a result of delivery localization.

Materials and procedures for forming liposomes are well-known to those skilled in the art and will only be briefly described herein. Upon dispersion in an appropriate medium, a wide variety of phospholipids swell, hydrate and form multilamellar concentric bilayer vesicles with layers of aqueous media separating the lipid bilayers. These systems are referred to as multilamellar liposomes or multilamellar lipid vesicles ("MLVs") and have diameters within the range of 10 nm to 100 $\mu$m. These MLVs were first described by Bangham, et al., *J. Mol. Biol.* 13:238–252 (1965). In general, lipids or lipophilic substances are dissolved in an organic solvent. When the solvent is removed, such as under vacuum by rotary evaporation, the lipid residue forms a film on the wall of the container. An aqueous solution that typically contains electrolytes or hydrophilic biologically active materials is then added to the film. Large MLVs are produced upon agitation. When smaller MLVs are desired, the larger vesicles are subjected to sonication, sequential filtration through filters with decreasing pore size or reduced by other forms of mechanical shearing. There are also techniques by which MLVs can be reduced both in size and in number of lamellae, for example, by pressurized extrusion (Barenholz, et al., *FEBS Lett.* 99:210–214 (1979)).

Liposomes can also take the form of unilamellar vesicles, which are prepared by more extensive sonication of MLVs, and consist of a single spherical lipid bilayer surrounding an aqueous solution. Unilamellar vesicles ("ULVs") can be small, having diameters within the range of 20 to 200 nm, while larger ULVs can have diameters within the range of 200 nm to 2 $\mu$m. There are several well-known techniques for making unilamellar vesicles. In Papahadjopoulos, et al., *Biochim et Biophys Acta* 135:624–238 (1968), sonication of an aqueous dispersion of phospholipids produces small ULVs having a lipid bilayer surrounding an aqueous solution. Schneider, U.S. Pat. No. 4,089,801 describes the formation of liposome precursors by ultrasonication, followed by the addition of an aqueous medium containing amphiphilic compounds and centrifugation to form a biomolecular lipid layer system.

Small ULVs can also be prepared by the ethanol injection technique described by Batzri, et al., *Biochim et Biophys Acta* 298:1015–1019 (1973) and the ether injection technique of Deamer, et al., *Biochim et Biophys Acta* 443:629–634 (1976). These methods involve the rapid injection of an organic solution of lipids into a buffer solution, which results in the rapid formation of unilamellar liposomes. Another technique for making ULVs is taught by Weder, et al. in "Liposome Technology", ed. G. Gregoriadis, CRC Press Inc., Boca Raton, Fla., Vol. 1, Chapter 7, pg. 79–107 (1984). This detergent removal method involves solubilizing the lipids and additives with detergents by agitation or sonication to produce the desired vesicles.

Papahadjopoulos, et al., U.S. Pat. No. 4,235,871, describes the preparation of large ULVs by a reverse phase evaporation technique that involves the formation of a water-in-oil emulsion of lipids in an organic solvent and the drug to be encapsulated in an aqueous buffer solution. The organic solvent is removed under pressure to yield a mixture which, upon agitation or dispersion in an aqueous media, is converted to large ULVs. Suzuki et al., U.S. Pat. No. 4,016,100, describes another method of encapsulating agents in unilamellar vesicles by freezing/thawing an aqueous phospholipid dispersion of the agent and lipids.

In addition to the MLVs and ULVs, liposomes can also be multivesicular. Described in Kim, et al., *Biochim et Biophys Acta* 728:339–348 (1983), these multivesicular liposomes are spherical and contain internal granular structures. The outer membrane is a lipid bilayer and the internal region contains small compartments separated by bilayer septum. Still yet another type of liposomes are oligolamellar vesicles ("OLVs"), which have a large center compartment surrounded by several peripheral lipid layers. These vesicles, having a diameter of 2–15 $\mu$m, are described in Callo, et al., *Cryobiology* 22(3):251–267 (1985).

Mezei, et al., U.S. Pat. Nos. 4,485,054 and 4,761,288 also describe methods of preparing lipid vesicles. More recently, Hsu, U.S. Pat. No. 5,653,996 describes a method of preparing liposomes utilizing aerosolization and Yiournas, et al., U.S. Pat. No. 5,013,497 describes a method for preparing liposomes utilizing a high velocity-shear mixing chamber. Methods are also described that use specific starting materials to produce ULVs (Wallach, et al., U.S. Pat. No. 4,853,228) or OLVs (Wallach, U.S. Pat. Nos. 5,474,848 and 5,628,936).

A comprehensive review of all the aforementioned lipid vesicles and methods for their preparation are described in "Liposome Technology", ed. G. Gregoriadis, CRC Press Inc., Boca Raton, Fla., Vol. I, II & III (1984). This and the aforementioned references describing various lipid vesicles suitable for use in the invention are incorporated herein by reference.

Current methods of manufacturing liposomes are typically batch processes. Attempts at large scale or continuous manufacturing have largely been unsuccessful, primarily due to the problems associated with mixing an aqueous liquid phase with the lipid phase and the need to maintain the lipid phase at a relatively constant temperature.

Accordingly, there is a need for an improved method for the production of liposomes, preferably one that can produce liposomes in a continuous fashion rather than by batch methods, without the variations and uncontrolled differences which make large scale production of liposomal preparations problematic. In addition, there is a need for an improved method and apparatus for producing other liquid compositions, including but not limited to emulsions, ointments and creams. Those needs are met by the instant invention.

SUMMARY OF THE INVENTION

The present invention relates to a method for the continuous production of a composition of matter, such as lipid vesicles, by in-line mixing, said method comprising: (a) preparing a first phase, such as a lipid phase, and storing the lipid phase in a first storage means that is maintained at a set temperature; (b) preparing a second phase, such as an aqueous phase, and storing the aqueous phase in a second storage means that is maintained at a set temperature; (c) combining the lipid and aqueous phases by means of a mixing device having first and second metering systems, a pre-mixing system and a mixer, such as a static mixer, by: transferring the lipid phase from the first storage means to the first metering system by a first pressurized transfer means and transferring the aqueous phase from the second storage means to the second metering system by a second pressurized transfer means; transferring the lipid phase from the first metering system to a first inlet orifice in the pre-mixing system by a third pressurized transfer means and transferring the aqueous phase from the second metering system to a second inlet orifice in the pre-mixing system by a fourth pressurized transfer means; wherein the lipid phase and aqueous phases are transferred to the pre-mixing system with a high velocity creating turbulent flow; combining the lipid and aqueous phases in the pre-mixing system by shear mixing under conditions to insure that the lipid phase becomes fully hydrated by the aqueous phase to form a pre-mixed formulation; and transferring the pre-mixed formulation from an outlet orifice of the pre-mixing system to the mixer, such as by a fifth pressurized transfer means or other suitable connection or fitting; (d) forming a mixed formulation comprising lipid vesicles, in the mixer by causing the pre-mixed formulation to traverse the mixer; (e) optionally measuring the optical properties of the lipid vesicles; and (f) dispensing the mixed formulation from the mixer into a storage chamber, into a means for further modification of the properties of the lipid vesicles, or into a means of packaging the mixed formulation.

In a second aspect, the invention relates to lipid vesicles and other compositions of matter produced by the method of the invention.

In yet another aspect, the invention pertains to a method of producing compositions such as lipid vesicles using an in-line mixing system, where an active agent is encapsulated in either the aqueous core of the lipid vesicles, within the lipid bilayer of the lipid vesicles, or both. In still another aspect, the invention relates to lipid vesicle encapsulated active agents produced by the method of the invention.

Another aspect of the invention pertains to an apparatus for the continuous production of a composition of matter such as lipid vesicles by in-line mixing, said apparatus comprising: (a) a first phase, such as a lipid phase, storage means capable of being maintained at a set temperature and a first pressurized transfer means for transferring the lipid phase from the storage means; (b) a second phase, such as an aqueous phase, storage means capable of being maintained at a set temperature and a second pressurized transfer means for transferring the aqueous phase from the storage means; (c) a mixing device comprising: a first metering system for receiving the lipid phase from the first pressurized transfer means; a second metering system for receiving the aqueous phase from the second pressurized transfer means; a pre-mixing system for preparing a pre-mixed formulation, having a pre-mixing chamber; a third pressurized transfer means for transferring the lipid phase from the first metering system to a first inlet orifice in the pre-mixing system and a fourth pressurized transfer means for transferring the aqueous phase from the second metering system to a second inlet orifice in the pre-mixing system; a mixer, such as a static mixer, for preparing a mixed formulation comprising lipid vesicles, having a mixing chamber and an optional means for determining the optical properties of the mixed formulation; a fifth pressurized transfer means or other suitable connection or fitting for transferring the pre-mixed formulation from the outlet orifice of the pre-mixing system to the mixing chamber; and an optional means for applying ultrasonic energy to the pre-mixing chamber, the mixing chamber or both of said chambers; and (d) a dispensing means for transferring the mixed formulation from the mixing chamber into a storage chamber, or into a means for further modification of the properties of the lipid vesicles or into a means of packaging the mixed formulation.

In another aspect, the invention relates to liposomes produced by the apparatus of the invention.

Still another aspect of the invention relates to the use of the method and apparatus described herein for the manufacture of emulsions, and the emulsions produced thereby.

BRIEF DESCRIPTION OF THE DRAWINGS

FIGS. 18 and 19 illustrate control panels for the invention.

FIG. 20 illustrates the bottom view of a power distribution module.

DESCRIPTION OF THE INVENTION

Figure 1:
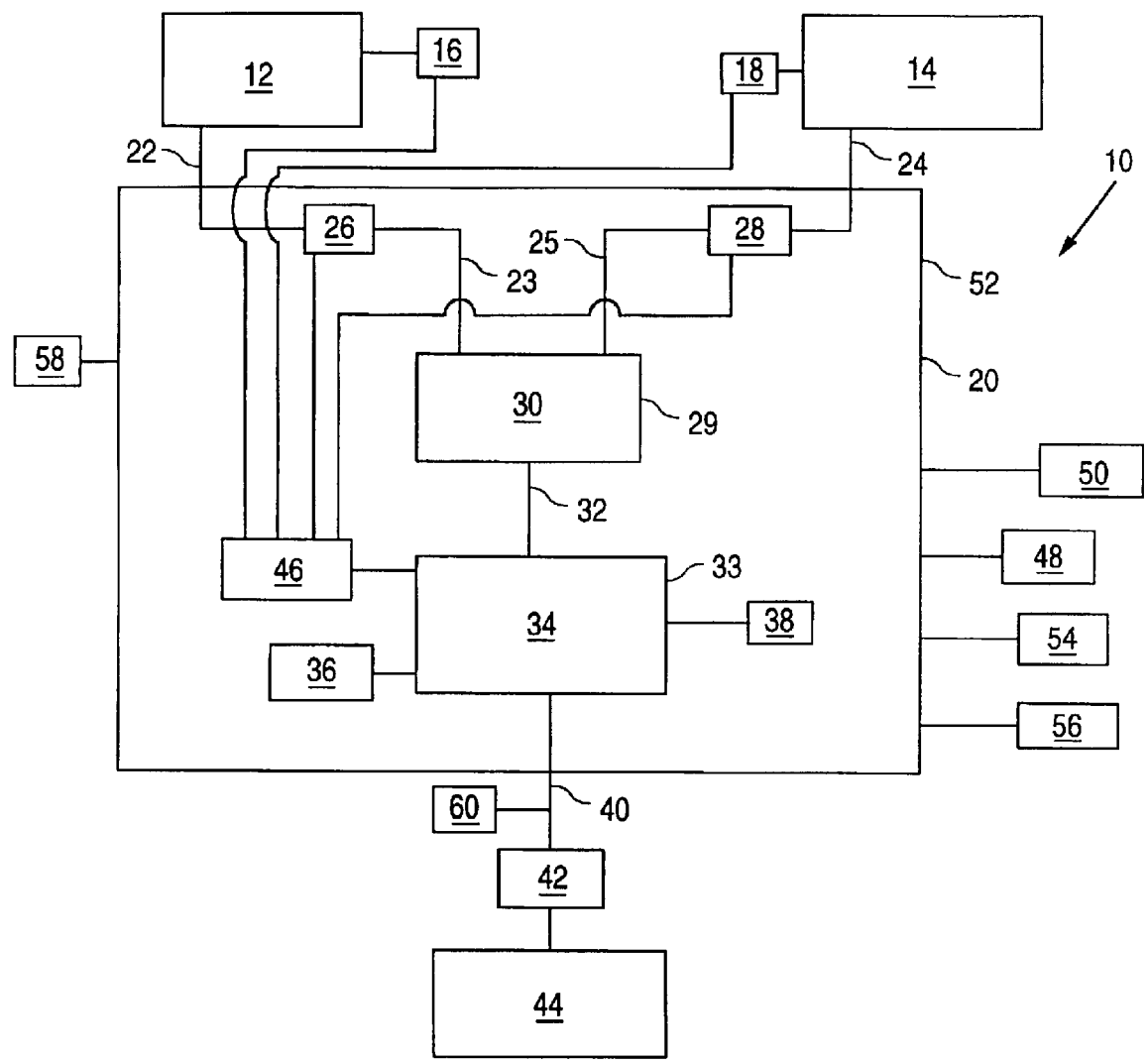
FIG. 1 is a schematic illustration of the invention.

The apparatus and method of the instant invention permits the flexible adaptation of a number of methods of production of lipid vesicles and other compositions of matter in a small space with a single device that can utilize a variety of production methodologies and techniques as dictated by the particular requirements of the product formula, any active agent to be incorporated into the composition and the application for which the final product is intended. For purposes of illustration only, the method and apparatus of the invention will be described for the production of lipid vesicles. However, the product and other compositions such as emulsions, ointments and creams are also contemplated by the invention.

Typically, an active agent is encapsulated in either the aqueous core of liposomes, within the lipid bilayer of the liposomes, or both, by dissolving or dispersing the agent in a lipid-containing organic solvent. However, the invention also contemplates the manufacture of lipid vesicles that do not contain any active agents. Such empty liposomes are currently used in cosmetic preparations and may be required as placebo material in clinical trials of therapeutic formulations. As used herein, the term "active agent" includes biologically active agents and is used to mean any molecule that acts as a beneficial or therapeutic compound, when administered to an animal, such that it prevents or alleviates a disease, arrests or alleviates a disease state or treats a disease in an animal, particularly a mammal, more particularly a human, and includes: preventing the disease from occurring in a subject which may be predisposed to the disease but has not yet been diagnosed as having it; inhibiting the disease, i.e. arresting its development; or relieving the disease, i.e. causing regression of the disease. Examples of active agents include by means of illustration and not limitation, anti-inflammatory agents; anti-cancer and anti-tumor agents; anti-microbial and anti-viral agents, including antibiotics; anti-parasitic agents; vasodilators; bronchodilators, anti-allergic and anti-asthmatic agents; peptides, proteins, glycoproteins, and lipoproteins; carbohydrates; receptors; growth factors; hormones and steroids; neurotransmitters; analgesics and anesthetics; narcotics; catalysts and enzymes; vaccines; genetic material such as DNA.

Although the products of the invention are particularly well suited for pharmaceutical use, they are not limited to that application, and may be designed for food use, agricultural use, for imaging applications, and so forth. Accordingly, the term "active agent" is more broadly used to mean any chemical or material that is desired to be applied, administered or used in a liposome formulation, and can include, by way of illustration and not limitation, pesticides, herbicides, cosmetic agents and perfumes, food supplements including vitamins and minerals, flavorings, and other food additives, imaging agents, dyes, fluorescent markers, radiolabels, plasmids, vectors, viral particles, toxins, catalysts, and so forth. The term "payload" is used herein to include active agents as defined above, along with any other ingredients that may be desirable to add to the product such as, by way of illustration and not limitation, diagnostic markers including radiolabels, dyes, chemiluminescent and fluorescent markers; contrasting media; imaging aids; and so forth. The payload can be a solid, liquid or gas.

Numerous phospholipids are useful in the manufacture of lipid vesicles, particularly those selected from the group consisting of phosphatidyl chlolines, lysophosphatidyl chlolines, phosphatidyl serines, phosphatidyl ethanolamines, and phosphatidyl inositols. Particularly suitable phospholipids are natural phospholipids such as soybean oil based phospholipids, for example the phosphatidylcholines, Phospholipon® 90H, 80H, 90G and 80G (American Lecithin Company, Oxford, Conn.), and Lecinol (Nikken). The phospholipid can be modified using a modifying agent such as a cholesterol, stearylamine or tocopherol. The solvent is then evaporated, usually under reduced pressure, to yield a thin lipid film containing the active agent. The lipid film is then hydrated, with agitation, using an aqueous phase containing any desired electrolytes and lipid vesicles containing the active agent are produced.

The invention relates to a method and apparatus that produces a very consistent reproducible, continuous and continuously variable output stream composed of liposomes in the form of multilamellar lipid vesicles ("MLVs"), unilamellar lipid vesicles ("ULVs") or oligolamellar vesicles ("OLVs") containing encapsulated active agents. As used herein, the terms "liposome" and lipid vesicle" are used interchangeably and are intended to include MLVs, ULVs and OLVs. The design of the equipment described herein is intended to allow constant monitoring of various factors that affect the size, distribution, structure, number and drug encapsulating efficiency of the vesicles so produced. The methods and embodiments described herein are typically capable of producing liposomal formulation at the rate of about 10 to 200 liters/hour, preferably 25 to 100 liters/hour. It is understood that these rates are merely illustrative of the rates attainable by the method and apparatus described herein. Lower rates may be desirable under certain circumstances, and higher rates may be attainable by standard optimization techniques, as are well known in the art, both of which are encompassed by the invention.

MLVs, ULVs and OLVs produced by state of the art methods tend to include a broad distribution of sizes and shapes as well as a broad range of payload volumes. Frequently, liposomal preparations include a substantial proportion of non-payload carrying vesicles. The invention consists of several innovations intended to consistently and controllably monitor and optimize the production of payload carrying MLVs, ULVs and OLVs, i.e., provides for higher encapsulation efficiency than state of the art methods with very reproducible results.

The instant invention pertain to an apparatus useful for the continuous production of a composition of matter by in-line mixing. In one embodiment of the invention, the apparatus comprises a first phase storage means capable of being maintained at a set temperature and a first pressurized transfer means for transferring the first phase from the storage means, along with an second phase storage means capable of being maintained at a set temperature and a second pressurized transfer means for transferring the second phase from the storage means. In a preferred embodiment, the first phase is a lipid phase (optionally containing an active agent) and the second phase is an aqueous phase. The lipid phase storage means is capable of being maintained at a set temperature by a first temperature control means, typically within the range of about 20 to 75° C. Similarly, the aqueous phase storage means is capable of being maintained at a set temperature by a second temperature control means, typically within the range of about 20 to 75° C. In one embodiment of the invention, the lipid phase and aqueous phase storage means are equipped with a means for continuously replenishing the lipid and aqueous phases. In this manner, the storage means function as a temperature stabilization means such that the lipid and aqueous phases are continuously fed into the storage means, where the temperature of each phase is stabilized prior to introduction into pressurized transfer means that exits each respective storage vessel.

The apparatus also has a mixing device that comprises a first metering system for receiving the lipid phase from the first pressurized transfer means, a second metering system for receiving the aqueous phase from the second pressurized transfer means, a pre-mixing system for preparing a pre-mixed formulation, a third pressurized transfer means for transferring the lipid phase from the first metering system to a first inlet orifice in the pre-mixing system and a fourth pressurized transfer means for transferring the aqueous phase from the second metering system to a second inlet orifice in the pre-mixing system. The pre-mixing system comprises a pre-mixing chamber having a first and second inlet orifice. In one embodiment of the invention, the pre-mixing system further comprises a means for creating turbulence in the aqueous phase prior to entry into the pre-mixing chamber.

The apparatus also has a mixer such as a static mixer for preparing a mixed formulation comprising lipid vesicles, having a mixing chamber and an optional means for determining the optical properties of the mixed formulation, a fifth pressurized transfer means for transferring the pre-mixed formulation from the outlet orifice of the pre-mixing system to the mixing chamber or other suitable connection or fitting; and an optional means for applying ultrasonic energy to the pre-mixing system, the mixing chamber or both. In a preferred embodiment, the optical properties of the mixed formulations are measured, with the means for determining the optical properties of the mixed formulation being configured so as to control the first and second temperature control means and the first and second metering systems.

Typically, the means for determining the optical properties will be in the form of an optical detector that consists of a light source, such as an incandescent bulb, light emitting diode or other suitable light emitting apparatus, which is positioned on one side of a chamber with parallel transparent windows. A sensor such as a photocell, phototransistor or photoresistor is positioned on the other side of the chamber, opposite the light source. The purpose of the optical detector is to generate a signal or value, such as resistance or voltage, that will vary in linear fashion in correlation to the opacity, translucency or other optical properties of the product, which vary with time, temperature, concentration and flow rates of the lipid and aqueous phase components. The signal thus derived, generated or measured, can then be used to activate transfer means, controls, pumps, motors, heaters, and so forth, through an interactive computer system, to maintain, alter, or adjust the properties of the product with greater precision. The signal can also be used to control and direct product flow to either a storage chamber, a means for packaging or to a waste receptacle, if for example, the product failed to meet desired specifications. One embodiment of the optical detector might include a diode that emits UV light that is absorbed by a specific active agent. In this manner, when the active agent is detected, the product flow is directed to a means for packaging; if the active agent is absent or present in an unsuitable amount, the product flow can be directed to a waste receptacle or the operation can be stopped so as to permit evaluation and correction of any problems.

The apparatus and method of the invention provide for lipid phase and aqueous phase streams that are as pulse-less as possible and are maintained at a constant pressure. This is a achieved by the precise metering systems described herein, each of which is provided with a pump that operates under positive pressure and in such a manner so as to provide precise volumetric delivery.

The mixer is preferably a static mixer, such as a laminar division type inline mixer. The mixer may have a means for controlling the temperature of the mixing chamber, which is typically within the range of about 20 to 80° C. In addition, the mixer may also have a means for controlling the degree and rate of mixing within the mixing chamber. The mixing device of the apparatus may also have a means for controlling the temperature within the open space of the mixing device, which is also typically within the range of about 20 to 80° C.

Finally, the apparatus has a dispensing means for transferring the mixed formulation from the mixing chamber into a storage chamber. This embodiment of the apparatus is particularly useful for the production of lipid vesicles, and more particularly multilamellar lipid vesicles. The apparatus of the invention is readily evaluated as to its particular suitability for manufacturing lipid vesicles having a pre-specified composition and configuration. Typically, two measurements are utilized to evaluate a method of manufacturing lipid vesicles: the encapsulated mass, the amount of encapsulated material/amount of lipid (wt material/wt lipid); and the captured volume, the amount of encapsulated aqueous phase/amount of lipid in vesicle (vol. aqueous/wt lipid).

In another embodiment, the apparatus also has a means for homogenization or sonication, which is located between the dispensing means and the storage chamber. This latter embodiment is particularly useful for the production of unilamellar lipid vesicles.

The apparatus may also have additional storage means for additional liquid phases such as a second lipid phase, a pre-mixed lipid phase-aqueous phase mixture, and/or a pre-formed lipid vesicle phase.

In operation, the apparatus of the invention typically operates under pressures within the range of about 10 to 90 psia, more commonly about 40–80 psia. It is understood that the apparatus and method of the invention are not necessarily operating under a constant pressure, and the actual pressure will vary among the components of the apparatus. The fluid flow rate of the lipid phase is usually about 3–200 $cm^3$/sec, more commonly 4 to 80 $cm^3$/sec. The fluid flow rate of the aqueous phases is usually about 5–300 $cm^3$/sec, more commonly about 10 to 100 $cm^3$/sec. The fluid flow rate at the various stages of the process and within the various components of the apparatus is determined by the initial flow rates, such that the flow rates of the lipid and aqueous phases remain constant and the flow rate of the mixed streams will be cumulative of the incoming lipid and aqueous rates. The fluid flow rate of the lipid phase is typically slower than that of the aqueous phase and will depend upon the desired composition of the product, i.e., the mixed formulation, but will usually be about 20–30% that of the aqueous phase. So, for example, for an aqueous fluid flow rate of about 20 $cm^3$/sec one may select a lipid fluid flow rate of about 6 $cm^3$/sec, which will then provide for a combined phase flow rate of about 26 $cm^3$/sec.

The dispensing means of the apparatus may have a means for controlling the rate at which the formulation is transferred from the mixing chamber into the storage chamber, which may be part of a packaging machine. This rate controlling means maintains the rate at which the mixed formulation is transferred.

In yet another preferred embodiment of the invention, each metering system contained within the apparatus has a precise metering pump and a manifold. Each pump and manifold has a plurality of inlet and outlet means, where each pump inlet means communicates with a manifold outlet means and each pump outlet means communicates with a manifold inlet means, The manifold, along with having a plurality of inlet and outlet means, also has a manifold outlet orifice and a manifold inlet orifice. In operation, the inlet orifice of a first manifold is in communication with the first pressurized transfer means and the outlet orifice of a first manifold is in communication with the third pressurized transfer means, the inlet orifice of a second manifold is in communication with the second pressurized transfer means and the outlet orifice of a second manifold is in communication with the fourth pressurized transfer means. The term "in communication with" is intended to mean connections such as: an inlet means that is configured so as to fit within an outlet means (or vice versa), an inlet means that is positioned immediately adjacent to an outlet means, and an inlet means that is connected to an outlet means by pipes, tubing or other suitable conduit that permits fluid flow, and so forth.

The various embodiments of the method and apparatus of the invention are best understood with reference to the Figures.

FIG. 1 is a schematic illustration of one embodiment of the apparatus of the invention for the production of compositions such as lipid vesicles, particularly MLVs, and also illustrates the method by which the liposomal formulation is produced. The apparatus 10 has individual means for storing each component of the formulation, each component being stored at a set temperature. The storage means are illustrated in FIG. 1 as vessels or reservoirs 12 and 14, which store the components of the formulation at specified temperatures, which are controlled by temperature controls 16 and 18. For example, one vessel may contain the lipid or lipid like phase and the other vessel might contain an aqueous phase, either one of which may contain one or more active agents or other payload.

It is understood, however, that although only two vessels are illustrated, the invention is not limited to that number and any number of storage means can be used, and the actual number will vary depending upon the number of components in the formulation. For example, a third vessel or reservoir may be used to add an additional lipid phase component to the formulation. Such an additional lipid phase would be added, for example, to facilitate the incorporation of one or more different, separately encapsulated active ingredients, or another form of phospholipid with a higher or lower melting point which would alter the properties of the mixture and would be added concurrently with, in advance of, or following the addition of the primary lipid phase to the aqueous phase in the pre-mixing system by means of an additional metering pump and at a point where it could be introduced either before, after or concurrently with the other streams. Similarly, an additional vessel (and metering pump) may be used to add a previously prepared two-phase mixture, for example, to incorporated a second or third active agent into the formulation, and would be added either concurrently with, in advance of, or following the addition of the primary lipid phase to the aqueous phase in the pre-mixing chamber.

The storage means useful in the method of the invention are typically vessels, reservoirs or tanks of any suitable configuration and can be made of any material that will withstand any temperature and pressure requirements and will not react with the components stored therein. Typical materials include, by way of illustration and not limitation, stainless steel, glass, suitable plastics, fluoropolymers, etc. The storage means can be large enough to store a sufficient amount of the components so as to enable production of a specified amount of formulation. On the other hand, the storage means 12 and 14 can function as mid-stream storage vessels that are continuously being replenished from an external source such as a larger vessel, not shown, as the components are being dispensed. In that manner, the amount of component stored within means 12 and 14 will remain relatively constant throughout the production cycle. The storage means may vary in size depending upon the individual needs of the process being run, however, they will typically hold from 0.5 to 15 liters, preferably from 1 to 1.5 liters, more preferably about 1.5 liters for a system that is not being replenished from an external source, and from 0.5 to 10 liters, preferably from 1 to 5 liters, more preferably about 5 liters for a system that is being replenished from an external source.

As indicated above, it is desirable to maintain the components of the formulation at set temperatures, which are controlled by temperature controls 16 and 18. These temperature controls can be commercially available discrete controllers as may be obtained from Omega Engineering, Inc. (Stamford, Conn.), programs running on a computer, or ladder type time, flow controlled controllers, and so forth.

The lipid and aqueous phases are typically maintained at a temperature within the range of 20–80° C. However, it may be desirable to maintain a slightly higher temperature for the lipid phase component. For example, a preferable range for the lipid phase might be about 55 to 65° C., more preferably about 60° C., while the corresponding temperature for the aqueous phase component would be within the range of about 50 to 60° C., more preferably about 55° C. The optimal temperature differential will be determined by the formulation itself and the desired product characteristics.

Each component is delivered to the mixing device 20 by pressurized transfer means 22 and 24, each of which is fitted with a precise metering system 26 and 28 to control the amount of material transferred from the storage means to the mixing device. Each metering system would typically comprise a pump, along with a manifold to control the pump output and input in order to eliminate any pressure pulsations of the component stream that would interfere with the precise mixing ratios needed for consistent product quality.

The mixing device 20 has a pre-mixing system such as a pre-mixer 29 having a pre-mixing chamber 30, where the individual components, i.e., the lipid phase and the aqueous phase are introduced under pressure by pressurized transfer means 23 and 25. Pressurized transfer means 22 and 24 transfer the formulation components from their respective vessels 12 and 14, to the precise metering systems 26 and 28. Pressurized transfer means 23 and 25 then transfer the formulation to the pre-mixing chamber 30. The mixing device may also be provided with a means, not shown, for establishing a gradient between the two component streams.

It is critical that the lipid and aqueous phases be transferred to the pre-mixing system with sufficient velocities such that turbulent flow is created in the pre-mixing chamber so as to provide shear mixing and to insure that the lipid phase becomes fully hydrated by the aqueous phase. For example, the lipid phase can be introduced to the aqueous phase by means of a concentrically centered hypodermic sized tube in the center of the tube carrying the aqueous phase. The interface between the two phases is such that the friction between the inner lipid stream and the outer aqueous stream creates laminar turbulence and eddy currents that will initiate the interfacial mixing process.

Transfer means 22, 24, 23 and 25 are typically configured as flexible tubing, stainless steel tubing, or as channels in a block of suitable material, and can be made of any non-corrosive, non-reactive materials including, by way of example and not limitation, plastic, rubber, aluminum, stainless steel, plastics, fluoropolymers such as Teflon and polyvinylidene fluoride (PVDF), etc.

The pre-mixer 29 is used for preparing a pre-mixed formulation and is designed to create a turbulent vortex in one component stream into which the second component stream is injected via high pressure. The combined component streams are then transferred via transfer means 32 and introduced into the mixer 33 having an in-line mixing chamber 34 of high shear, high pressure design. Transfer means 32 can be of a configuration and materials such as described above for transfer means 22, 24, 23 and 25. Preferably transfer means 32 is a relatively short fitting that serves to connect the outlet of the pre-mixer with inlet of the mixer or may simply be the juncture of the pre-mixer outlet and mixer inlet such as when the outlet of the pre-mixer is positioned adjacent to and communicates with the inlet of the mixer.

The length of the mixing chamber 34 can be varied to control the number of laminar divisions that the stream passes through. The mixer 33 is preferably a static mixer. As used herein the term "static mixer" is used to refer to a mixer whose internal chamber creates turbulence in the fluid flow by the presence of, for example, a spiral or baffled interior casing, such that movement of the component streams through the mixer creates a mixed product, without the need for any moving parts in the mixer. Suitable static mixers include laminar division type inline mixers or an inline static ISG (Interfacial Surface Generator) mixing device, which has either a stream division or intercalated spiral baffle design. Commercially available static mixers that are suitable for use in the instant invention include the TAH 70, 85, 100, 120 and 160 Series motionless mixers sold by TAH Industries, Inc. (Robbinsville, N.J.), and the ISG motionless mixer sold by Charles Ross & Son Company (Hauppauge, N.Y.).

The mixing chamber 34 is equipped with a means 36 for controlling the temperature of the chamber. It is preferable to maintain the temperature of the mixing chamber within the range of about 20 to 80° C., preferably 50 to 70° C., more preferably about 60° C. The temperature controlling means 36 is typically a discrete thermocouple, a platinum thermocouple type automatic controller, a ladder type controller, or a control routine operating on a computer. The mixing chamber 34 is also equipped with a means 38 for controlling the degree and rate of mixing within the chamber. This mixing controlling means 38 is typically a means for moving the lipid and/or aqueous phase transfer means in and out of the chamber to adjust the insertion point for the desired degree of turbulence. Also a means may be provided for adjusting the angle of the transfer means relative to the wall of the mixing chamber to enhance or decrease the rotational turbulence thereby induced.

After the formulation is mixed, it is dispensed via dispensing means 40, which is equipped with a control means 42 for controlling the rate at which the formulation is transferred from the mixing chamber 34 into the storage chamber 44. The storage chamber can be part of a packaging machine, not shown. The mixed formulation can be used as is, without the need for any solvent removal.

Dispensing means 40 is typically configured as a sanitary valved outlet, and can be made of any non-corrosive, non-reactive materials including, by way of example and not limitation, plastic, rubber and aluminum.

The flow rate controlling means 42 typically operates by adjusting the stepping rate of the motors controlling the pumps as well as the sizes of the orifices in the manifolds, and controls the flow rate so that it is maintained within the desired range.

Along with delivering all of the product to the storage chamber 44, the invention also contemplates that the device be equipped with a means for diverting the output stream from chamber 34 to either of two or more chambers or channels, thereby providing a mechanism whereby product may diverted from the primary flow to the storage chamber 44 if the sensors determine it to be below acceptable quality levels, until the sensors can shut the device down.

The mixer 33 is also equipped with a determining means 46, which can be one or more detectors that operate by use of a feedback system so that each respective detector is connected to or configured so that it controls the temperature controlling means 16 and 18 and the metering systems 26 and 28. One such detector can be an optical sensor for determining the optical properties of the mixture within chamber 34 for purposes of adjusting the temperature and flow rate of the components for optimum product quality. A certain degree of opacity is the indication of successful mixing. If the material develops a transparency and transmits more light than is expected, this is determined by a simple photoresistor or phototransistor detector circuit, and the controlling mechanism is instructed to divert the stream and or shut down the system. Another detector can be a rheometric device, or viscometer, that determines the viscosity of the mixture for further process quality monitoring and control. As with the optical sensor, the rheometric device would also be able to control the temperature controlling means 16 and 18 and the metering systems 26 and 28, so as to adjust the temperature and flow rate of the components.

The mixing device 20 may be equipped with a means 48 of applying ultrasonic energy to the pre-mixing chamber 30 and/or the mixing chamber 34. Use of ultrasonic energy in the formation of lipid vesicles is described, for example, in Gersonde, et al., U.S. Pat. No. 4,452,747; Huang, *Biochemistry* 8:344(1969); Papahodjopoulos, et al., *Biochim Biophysica Acta* 135:624 (1967); Schneider, U.S. Pat. No. 4,089,801; and Hsu, U.S. Pat. No. 5,653,996, the disclosures of which are incorporated herein by reference.

The purpose of the ultrasonic energy is to facilitate formation of a desirable vesicle size and/or size distribution. Ultrasonic energy can be applied by means of a transducer that is in direct contact with various metal surfaces of the pre-mixing chamber. Depending on the placement of the transducer relative to the point at which the lipid phase and the aqueous phase make contact, the application of ultrasonic energy can be used to either aid in the formation of multilamellar liposomes or to help convert the multilamellar vesicles into unilamellar vesicles of certain constrained size ranges.

The process by which large unilamellar and multilamellar vesicles may be converted to smaller multilamellar and or unilamellar vesicles is described by Gregoriadis (CRC Press), supra. The multilamellar liposomes produced by the method and apparatus of the invention are typically within the range of 10 nm to 100 µm, and are preferably about 0.2 to 25 µm, more preferably about 0.5 to 20 µm in diameter. Preferably the small unilamellar liposomes produced by the method and apparatus of the invention are about 20 to 200 nm in diameter, while the larger unilamellar liposomes produced by the method and apparatus of the invention are about 200 nm to 2 µm in diameter.

In addition, application of ultrasound also serves to induce more uniformity in the size and distribution of the vesicles, relative to the frequency at which the ultrasonic energy is being transmitted. Suitable means for accomplishing this include any means for generating high-frequency electric energy, such as generators, sonicators, ultrasonic homogenizers and tissue disruptors. For example, high frequency electric energy is supplied from an electric generator, then converted into ultrasonic energy or vibrations and transmitted by an ultrasonic transmitter into one or both of the mixing chambers.

The mixing device 20 is also equipped with a means 50 for controlling the temperature of the apparatus, in particular for controlling the temperature of the open space surrounding the various components of the apparatus such as the transfer means, pre-mixing system and mixer. The temperature controlling means 50 is similar in form and function to the temperature controlling means 36 described above. It is preferable to maintain the temperature within the interior of the mixing device within the range of about 20 to 80° C., preferably about 50 to 70° C., more preferably about 60° C., in essence a temperature close to that within the mixing chamber 58.

The components of the mixing device 20 can be encased in a sealed container 52, which can replicate a "clean room" such as is necessary in the production of pharmaceuticals, for example. Container 52 would be featured with inlet 54 and outlet 56 valves as a method of sterilizing and sanitizing the entire outside surfaces of the components contained therein such as the metering systems and pre-mixer and mixer components such as their respective chambers, along with the inside surface of the container itself. Steam, ethylene oxide or liquid sterilants are suitable for use as sterilizing or sanitizing agents to be delivered by inlet valve 54, and subsequently removed by outlet valve 56. The device 20 would also be equipped with cleaning means 58 by which the interior of the components contained therein such as the metering systems and pre-mixing and mixing chambers could be cleaning, such as by the introduction of heated cleaning agents such as chlorohexidine, sodium hypochlorite, soaps, detergents, ethanol water mixtures, and so forth.

The apparatus 10 may also be equipped with a heating/cooling means 60, positioned external to the mixing device 20. The dispensing means 40 can be shaped to extend beyond the periphery of the mixing device and fitted with such a heating/cooling means, which can be configured as a jacket surrounding the dispensing means having a cooled or heated fluid flowing within.

A slight modification of the schematic illustration of FIG. 1 provides another embodiment of the apparatus of the invention for the production of liposomes, and is particularly suited for the production of ULVs. After the formulation is mixed in chamber 34, it is dispensed via dispensing means 40 and control means 42. However, before being directed to a storage chamber or packaging machine, the formulation is subjected to high pressure in-line homogenization or sonication, thereby causing the vesicles to be reduced in size or causing them to agglomerate, resulting in a uniform sizing. After this process is complete, the formulation is then directed to the storage chamber or packaging machine.

Figure 2:
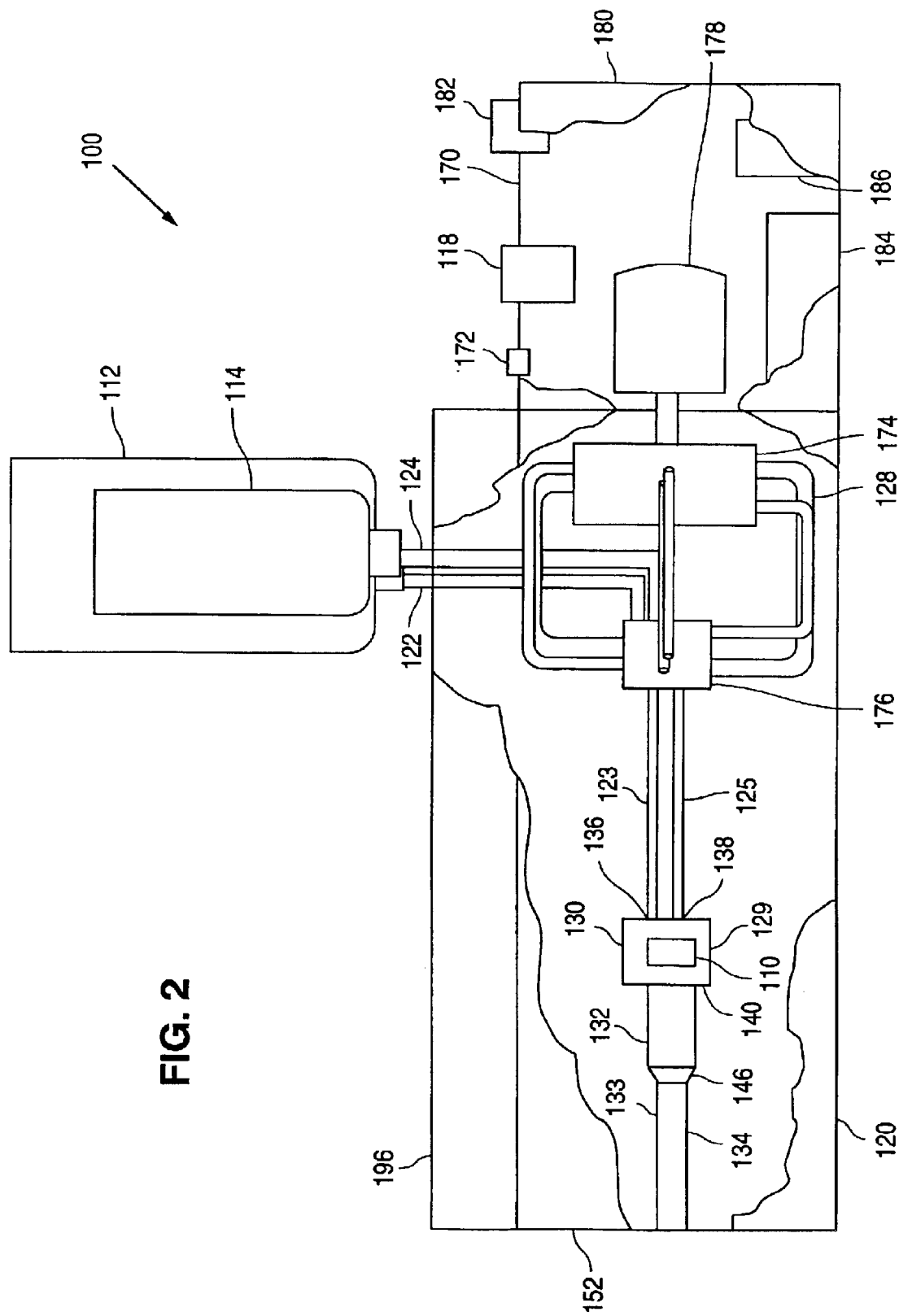
FIG. 2 is cut-away side view of one embodiment of the invention.
Figure 3:
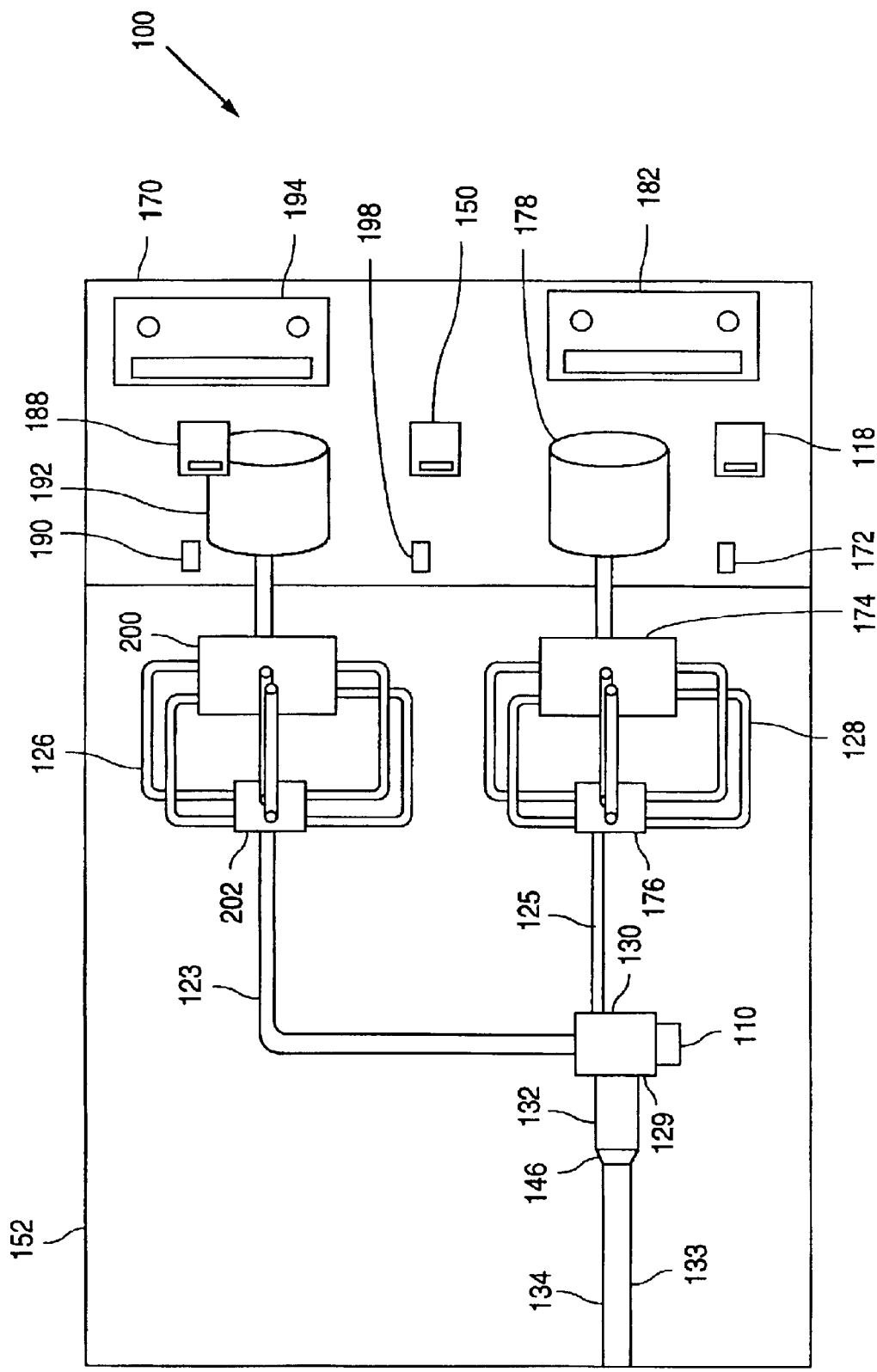
FIG. 3 is a top view of the embodiment shown in FIG. 2.

One embodiment of the invention is illustrated in FIGS. 2 and 3, where FIG. 2 is a cut-away side view and FIG. 3 is a top view. The apparatus 100 has four main parts: individual means for storing each component of the formulation 112 and 114, a sealed container 152, encasing the various parts of the mixing device, and an open box 170, which holds the control elements as will be described below.

The larger vessel 112 would typically be used to store a first liquid phase, such as an aqueous phase component and the smaller vessel 114 would typically be used to store a second liquid phase, such as a lipid phase component. It is desirable to store each component at a set temperature and this is readily accomplished by means of temperature controls. Temperature control 118, which controls the temperature of vessel 114, is shown in FIG. 2. Temperature control 118 could be a discrete thermocouple based controller as is available from Omega Engineering, Inc., for example, and would be connected to power source 172, for example, an electrical outlet.

Each component is delivered to the mixing device 120 by pressurized transfer means 122 and 124, each of which is fitted with a precise metering system 126 and 128 to control the amount of material transferred from the storage means to the pre-mixing chamber 130. Metering system 128 is shown in FIG. 2 as comprising a precise metering pump 174, along with a manifold 176 to control the pump output and input in order to eliminate any pressure pulsations of the component stream that would interfere with the precise mixing ratios needed for consistent product quality. Essentially, the manifold serves to convert a pulsed input from the pump to an unpulsed output by means of phase compensation. The metering system is driven by a motor 178 such as a stepper motor.

The mixing device 120 has a pre-mixing system such as a pre-mixer 129 having a pre-mixing chamber 130, where the individual components are introduced under pressure by pressurized transfer means 123 and 125. Accordingly, the pre-mixing chamber has a first inlet orifice 136 connected to transfer means 123 for inlet of the aqueous phase, a second inlet orifice 138 connected to transfer means 125 for inlet of the lipid phase, and an outlet orifice 140 connected to transfer means 132. The pre-mixer is designed to create a turbulent vortex, whereby one component stream is injected by means of high pressure into a second component stream or both streams are injected by means of high pressure.

The pre-mixed formulation is then transferred by transfer means 132 and introduced into a mixer 133 having, for example, a laminar division type inline mixing chamber 134 of high shear, high pressure design. After the formulation is mixed, it is dispensed via dispensing means into a storage chamber or a means for packaging such as a packaging machine, not shown. In addition; the invention also contemplates use of a means for further modification of the properties of the liposomes, which would be positioned immediately after the dispensing means. Such means for further modification can be, for example, a means for homogenization or sonication. This would enable one to make a ULV-containing formulation from a MLV- or OLV-containing formulation. The modified formulation could then be dispensed into a storage chamber or a means for packaging, as indicated above for the mixed formulation.

However, the modified formulation could also be used in a separate apparatus. It could be placed in a storage vessel and, with its own metering system, be used as a third component in another formulation.

As indicated above, the apparatus 100 includes a box 170 that has an open end 180 to permit access to the power components, electrical systems, etc. Along with the temperature control 118, power source 172 and motor 178, this box also houses an indexer 186 that controls the motor 178, an indexer controller 182 for controlling the indexer 186, and a relay 184 for controlling the temperature control 118.

FIG. 2 only shows the components that are connected to metering system 128. Metering system 126, shown in FIG. 3, has similar components that relate to its performance. FIG. 3 illustrates the temperature control 188, power source 190, motor 192, and indexer (not shown) that controls motor 192, an indexer controller 194, and a relay (not shown) all of which work with metering system 126. There also is a relay (not shown) for controlling the temperature control 150.

Container 152 is sealed by means of a cover or lid 196 that is removable, but bolted in place, and preferably includes a rubber seal, for example, to provide for a tightly sealed system during operation. The container can also be sealed by numerous means, including by way of example and not limitation, clamps, drawing a vacuum in the case of sensitive ingredients, and by means of a lip and channel configuration.

The mixing device 120 is equipped with a generator 110, as means of applying ultrasonic energy to the pre-mixing chamber 130 and/or the mixing chamber 134. In the embodiment shown in FIGS. 2 and 3, the generator 110 is shown as being mounted on the pre-mixing chamber 130, an appropriate position when ultrasonic energy is being directed to the pre-mixing chamber. It is understood however, that the generator can be mounted on the transfer means 132 if it is desired to direct energy to the mixing chamber 134. This latter configuration can be in lieu of or in addition to the generator mounted on the pre-mixing chamber.

FIG. 3 provides another view of this embodiment of the invention. This view shows that the mixing device is also equipped with a means 150 for controlling the temperature of the device, and a power source 198. Also shown in FIG. 3, is a top view of metering system 126 which comprises a precise metering pump 200, along with a manifold 202. The metering system is driven by a motor 194 as noted above.

One skilled in the art will recognize other comparable parts that can be assembled in the manner shown in FIGS. 2 and 3 to produce a liposomal formulation in the manner described herein. In particular, suitable precise metering pumps are well known in the art. Particularly well suited for the method and apparatus of this invention is the Travcyl™ metering pump (Encynova International, Inc., Broomfield, Colo.), which provides the accurate and efficient fluid delivery required by this invention. A simplified version of this pump is shown in FIGS. 4 and 5.

Figure 4:
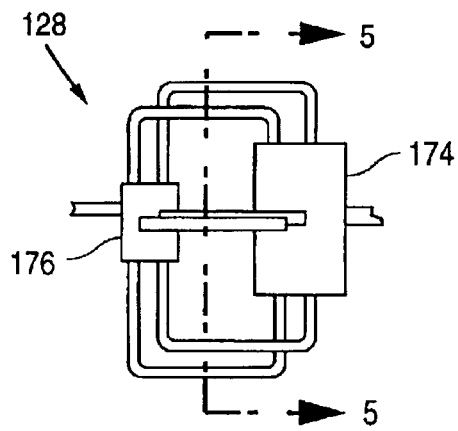
FIG. 4 illustrates one embodiment of the metering system of the invention.

FIG. 4 shows one embodiment of the precision metering system 128 of the invention, having a precise metering pump 174 and manifold 176. The pump and manifold are typically provided with a plurality of inlets and outlets. The manifold has a plurality of inlets and outlets that correspond to the number of outlets and inlets on the pump. In addition, the manifold has an inlet whereby lipid or aqueous phase is transferred from the storage vessel and an outlet whereby the formulation components is transferred to the pre-mixing system.

Figure 5:
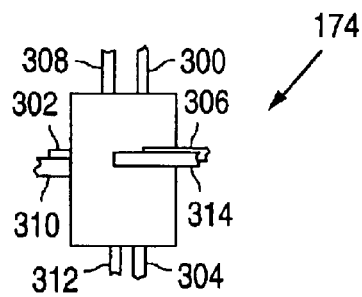
FIG. 5 is a cross-sectional view of a metering pump, taken along line 5—5 of FIG. 4.

A pump 174 having four inlets and four outlets is illustrated in FIG. 5. The formulation component is transferred from its storage vessel 114 to the manifold 176 via pressurized transfer means 124 prior to entering the pump. The component is transferred to the pump by pump inlet means 300, 302, 304 and 306. The component then returns to the manifold 176 by pump outlet means 308, 310, 312 and 314, and then exits the manifold by pressurized transfer means 125 for delivery to the pre-mixing chamber 130. The pump inlet and pump outlet means are typically comprised of a flexible tubing material such as Teflon, PVDF, polypropylene, stainless steel tubing or armored polymer tubing. Pump inlet 300 and pump outlet 308 are both connected to one of four cylinders in pump 174. Similarly inlet/outlet pairs 302/310, 304/312 and 306/314 are connected to the remaining three cylinders, respectively.

Figure 6:
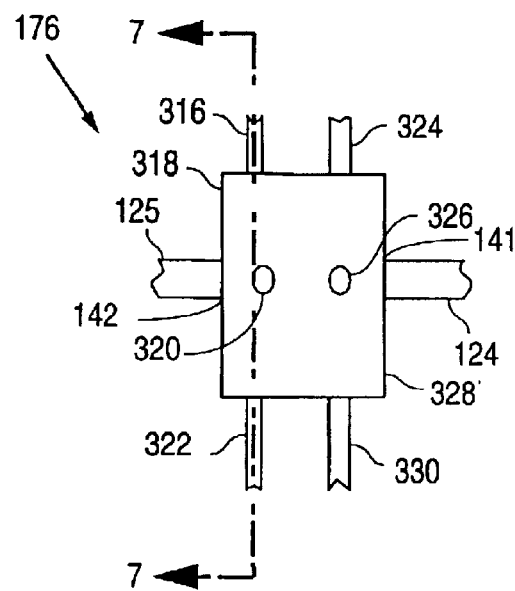
FIG. 6 illustrates one embodiment of a manifold.

FIG. 6 illustrates one embodiment of a manifold 176 useful in combination with the pump 174 of FIG. 5. Similar to the pump, the manifold is provided with four inlets and four outlets, which are numbered and identified separately. Each pump outlet means communicates with a manifold inlet means, and each pump inlet means communicates with a manifold outlet means. In addition, the manifold has an inlet orifice that communicates with the storage vessel and an outlet orifice that communicates with the pre-mixer, as described in detail below.

Figure 7:
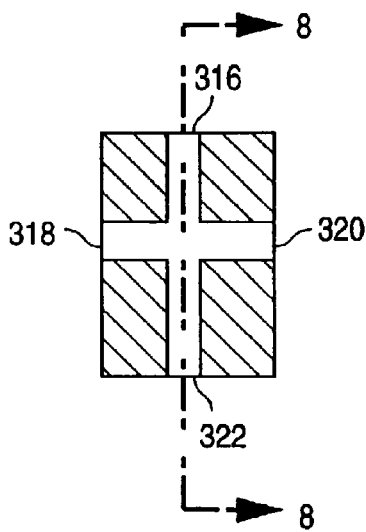
FIG. 7 is a cross-sectional view of a manifold, taken along line 7—7 of FIG. 6.
Figure 8:
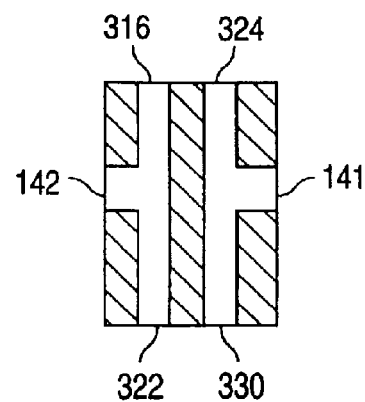
FIG. 8 is a cross-sectional view of a manifold, taken along line 8—8 of FIG. 7.

Referring now to FIG. 6, the formulation component is transferred from its storage vessel 114 to the manifold via pressurized transfer means 124 at manifold inlet orifice 141. The component is then transferred to the pump by manifold outlet means 324, 326, 328 and 330, where manifold outlet 328 is on the back side. The component then returns from the pump to the manifold by manifold inlet means 316, 318, 320 and 322, where manifold inlet 318 is on the back side, and then exits the manifold by pressurized transfer means 125 at manifold outlet orifice 142 for delivery to the pre-mixing chamber. The manifold can be for example, a solid block in which the four inlet means are laterally bored holes, as illustrated in FIG. 7. The same configuration holds for the four outlet means. An axially bored hole that meets at the junction of the four inlet means forms the manifold outlet orifice 142 connecting the pressurized transfer means 125 to the manifold. Similarly, an axially bored hole that meets at the junction of the four outlet means forms the manifold inlet orifice 141 connecting the pressurized transfer means 124 to the manifold. This is illustrated in FIG. 8.

In operation, the two component, i.e., precursor phases provided for in the formulation are each prepared and heated to the proper temperatures, at which time they are transferred to the apparatus 100. Typically, Phase I of the mixture (the aqueous phase) is prepared and heated and is introduced into the larger of the two vessels 112, which has been preheated to the required temperature before filling. Phase II of the mixture (the lipid phase) is prepared and heated, is then introduced into the smaller vessel 114 which has also been preheated to the required temperature. Once stored in the pre-heated vessels 112 and 114, the phases are maintained at the required temperature, via individual feedback and control systems. The apparatus is equipped with two pumps 174 and 200, each of which is equipped with four positive pressure, positive displacement pumping chambers.

The four inputs from each pump are combined through the use of unique manifolds 176 and 202. The four outputs of each pump are then pumped through the same respective manifold and then transferred in a precise ratio to the pre-mixing chamber 130. The result is a near or virtually pulse-less flow, which permits of precise metering ratios of the two components, i.e., the lipid and aqueous phases that constitute the liposomal formulation. The two components are each individually pumped through the use of the near "pulse-less" precision metering pumps 174 and 200 into the premixing chamber 130 where they are introduced to each other in a precise ratio. The two phases are then introduced into the inline mixing chamber 134 of appropriate length, diameter and composition for the specific product to be manufactured.

The near "pulse-less" action is the pump is achieved by use of the four pump inlet means, each of which is 90° out of phase with the preceding inlet means and the successive inlet means. For example, referring to the pump 174 shown in FIG. 5, there are four inlet means shown, 300, 302, 304 and 306. The operation curve of inlet means 302, for example, is out of phase by 90° from the operation curve of inlet means 300 and 304, and so forth. In operation then, these curves cancel each other out to provide for continuous, near "pulse-less" flow of the component from the vessel 114, to the manifold 176 to the pump 174, back to the manifold 176, then on to the pre-mixing chamber 130.

The two phases can be slightly intermixed in an interfacial juncture in the pre-mixing chamber 130, from which they are then forced through transfer means 132 into the static mixer 134. The design of the pre-mixing chamber incorporates surfaces that create specific turbulence patterns that have very specific effects on the properties of the liposomes during their formation. In addition, various baffles may be added to the pre-mixing chamber or machined into the inner surface of the chamber, to increase turbulence.

The design of the pre-mixing chamber 130 and the mixing device permit the use of an ultrasonic generator to be used on either or both of the chambers. The frequency and signal power of the generator can be controlled by the same computer that monitors and controls the temperatures of the supply vessels, the temperature of the enclosure and the mixing chambers, and the flow rates of the two precision metering pumps.

The length and internal components of the mixing chamber 134 are selected so as to maximize the effectiveness of the mixing process, as described above.

The mixer feeds product through a determining means 146 which can be a sensing device or detector where the optical properties of the product are measured and the results supplied to a monitoring and process control system, which is responsible for the monitoring and adjustment of temperature, flow rate and mixing proportions of each of the two phases based on sensor values, programmed responses and operator input. The monitoring and process control system typically involves suitable sensor and readout display devices, and the necessary adjustments can be made manually by the operator or the entire system can be readily computerized by methods as are well known in the art.

Figure 9:
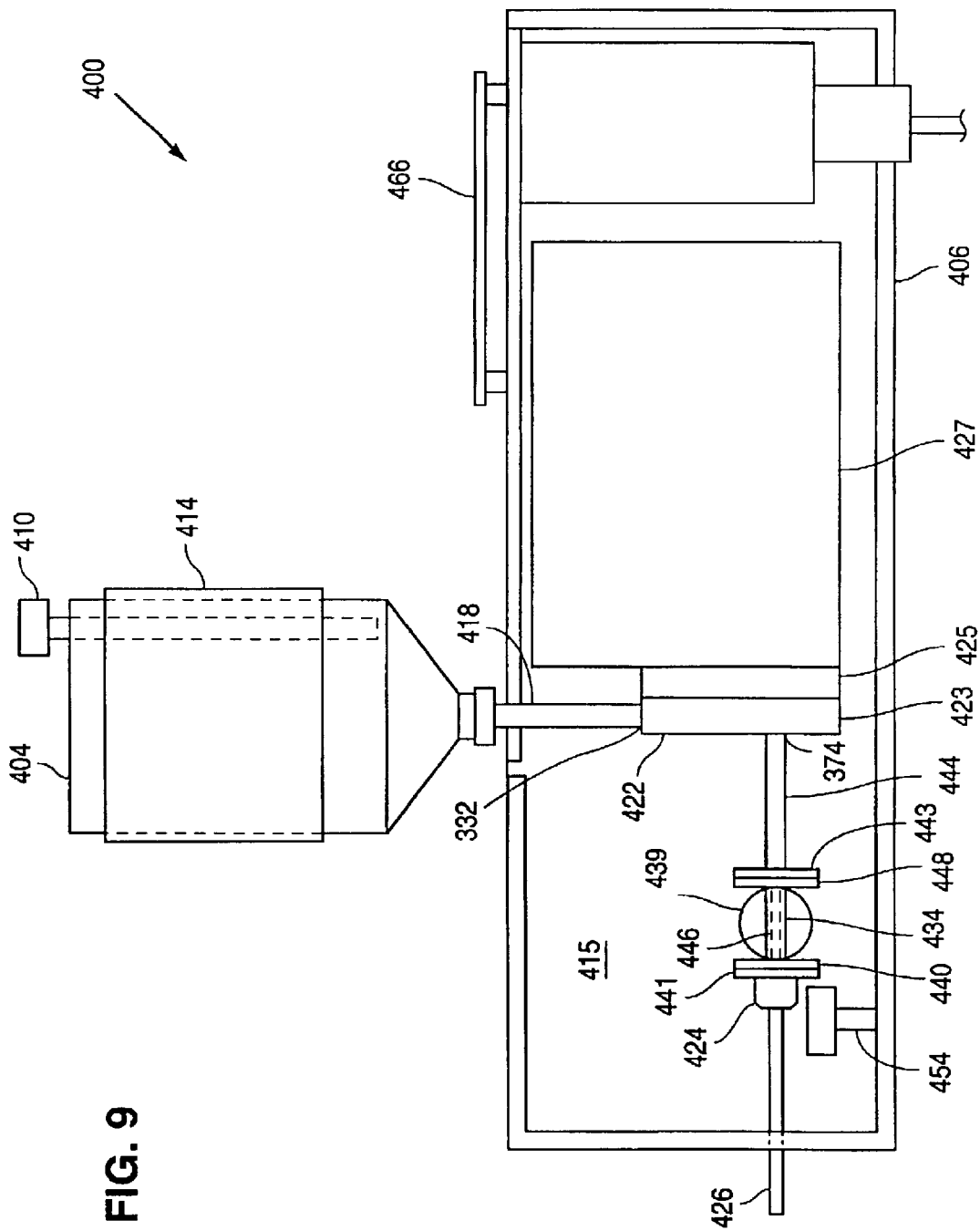
FIG. 9 is cut-away side view of another embodiment of the invention.
Figure 10:
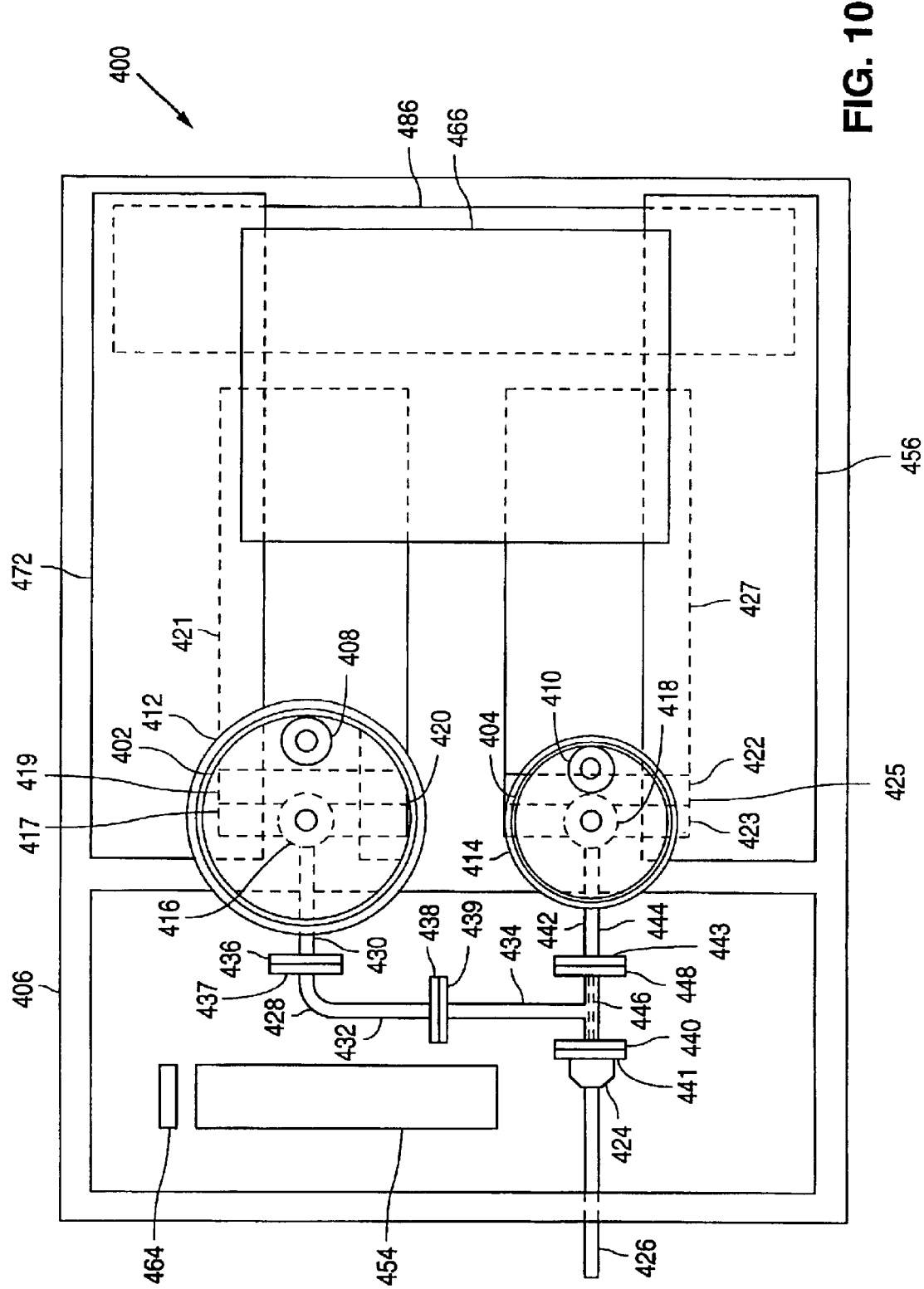
FIG. 10 is a top view of the embodiment shown in FIG. 9.

Another embodiment of the invention is illustrated in FIGS. 9 and 10, where FIG. 9 is a cut-away side view and FIG. 10 is a top view. This embodiment illustrates some variations on the embodiment of FIGS. 2 and 3, and it is understood that the invention encompasses other combinations of these two embodiments. In particular, the embodiment of FIGS. 9 and 10 illustrate one means by which temperature of the storage vessels can be monitored and maintained, an alternate manifold and an alternate pre-mixing system for the aqueous and lipid phases, along with illustrating one embodiment of means by which the entire operation can be run, monitored and controlled.

Referring now to FIGS. 9 and 10, the apparatus 400 is equipped with individual means for storing each component of the formulation 402 (larger vessel to store the aqueous phase components) and 404 (smaller vessel to store the lipid phase component), and a sealed container 406, encasing the various parts of the mixing device 415 and the control elements.

The temperature of each storage vessel is controlled by individual temperature sensors 408 and 410, along with heating elements 412 and 414. Each temperature sensor is inserted into the fluid contents of its respective vessel. One preferred type of temperature sensor is a platinum resistance temperature sensor device, as such devices are well suited to precisely maintaining the temperature of the contents at a set temperature. The heating element is configured to wrap around the exterior of the individual vessel and is typically a thermal foil heater comprised of a heating element encapsulated within a flexible silicone rubber jacket.

Each component is delivered to the mixing device 415 by pressurized transfer means 416 and 418 to individual precise metering systems 420 and 422 to control the amount of material transferred from the storage means ultimately to the pre-mixing chamber 424, and then to the in-line mixer 426. Precise metering system 420 comprises a manifold 417 and a precise metering pump 419. The system also includes housing 421, which contains a motor, controller and power supply. Similarly, precise metering system 422 comprises a manifold 423, precise metering pump 425, and similar housing 427. Details of this embodiment of the pre-mixing system of the invention will be described in detail below.

The pre-mixing system of this embodiment is best illustrated with reference to FIG. 10. The aqueous phase exits the precise metering system 420 by pressurized transfer means 428, which is illustrated as having a straight section 430, an L-fitting section 432, and a T-shaped section 434, connected by coupler flanges 436, 437, 438 and 439. The T-shaped section 434 is connected to the pre-mixing chamber 424 by coupler flange 440 and coupler flange 441 on the pre-mixing chamber, joined with a silicone gasket and clamp. The lipid phase exits the precise metering system 422 by pressurized transfer means 442, which has a straight section 444 having a diameter approximating that of the sections of pressurized transfer means 428, and an injector section 446 having a smaller diameter than the sections of pressurized transfer means 428. The sections of pressurized transfer means 428 are attached to each other and joined to section 434 by means of coupler flange 448. The injector section 446 extends within the T-portion of section 434 and exits directly into the pre-mixing chamber 424.

Figure 11:
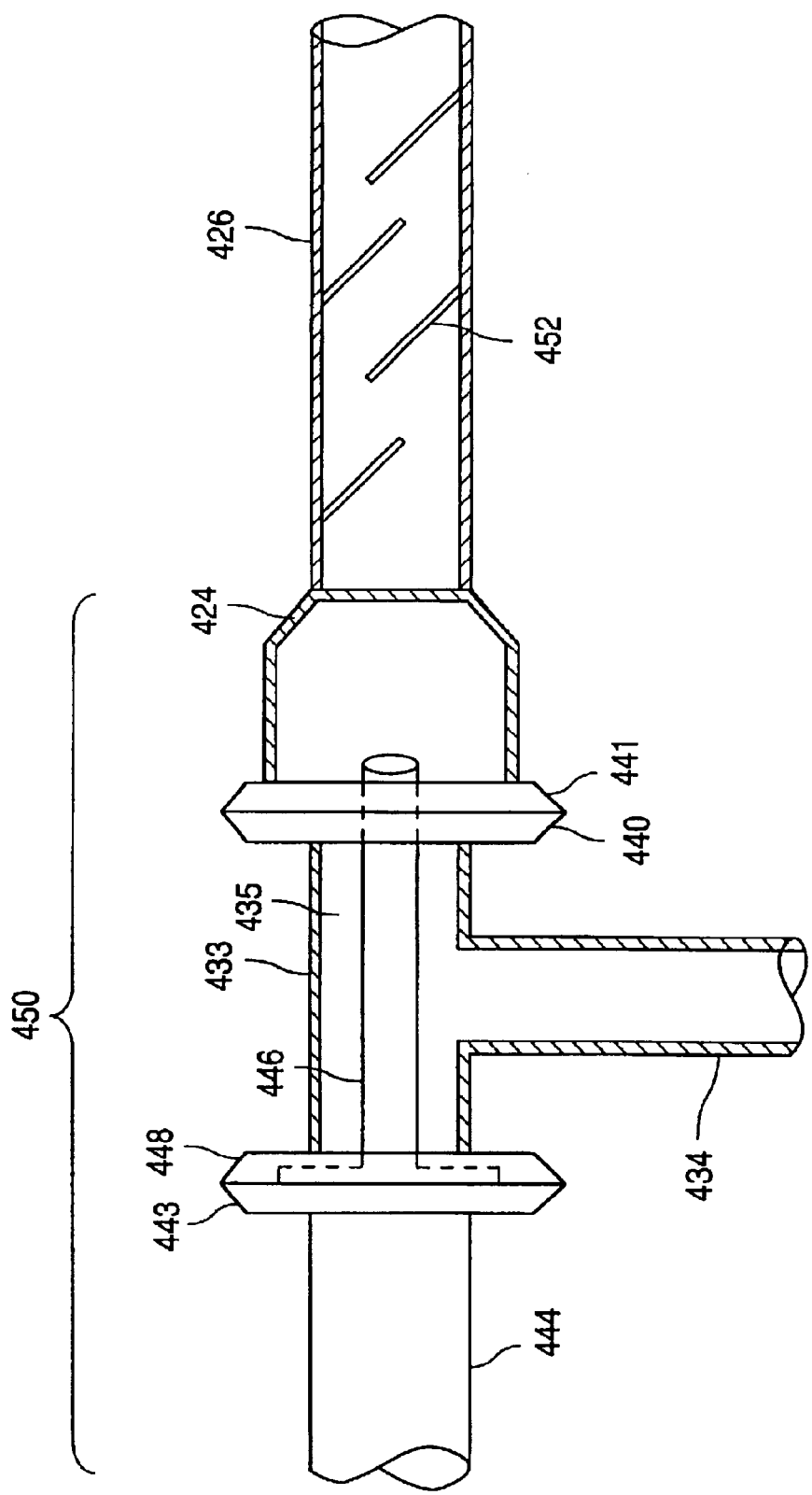
FIG. 11 is a partial cross-section of one embodiment of the pre-mixer system.

In operation, the aqueous phase exiting the straight portion of T-shaped section 434 encounters the exterior length of the injector section 446 and turbulence is created before the aqueous phase enters the pre-mixing chamber 424, where it is mixed with the lipid phase entering the chamber via injector section 446. This is illustrated in FIG. 11, which shows a partial cross-section of the pre-mixing system 450. This configuration of the juncture of the aqueous phase pressurized transfer means 428 and the lipid phase pressurized transfer means 442 illustrates one embodiment of the invention by which the lipid and aqueous phases can be introduced in a precise manner and provide for temperature stabilization due to concentric flow.

Turbulence is introduced into the aqueous phase within the branched portion 433 of the T-shaped section 434. The injector section 446.fits snugly into the recess of the flange 448 of the T-shaped section 434, and prevents backflow of the aqueous phase in to the straight section 444 of the lipid phase pressurized transfer means 442. The straight section 444 is connected to the T-shaped section by coupler flange 443. The recursive flow of the aqueous phase into the chamber 435 of the branched portion 433 creates a damping effect. The ratio of (a) the internal cross-sectional area of the branched portion 433 which is not occluded by injector section 446 to (b) the internal cross-sectional area of injector section 446 is determined by the desired volumetric ratio of the aqueous phase to the lipid phase for any given formulation.

FIG. 11 also illustrates the cross-section of a suitable configuration of the in-line mixer 426, as having a plurality of baffles 452. However, it is understood that this invention is not limited to this configuration and any suitable configuration of the in-line mixer is encompassed by the invention, as long as turbulent mixing of the aqueous and lipid phases is achieved.

Referring again to FIG. 10, the apparatus 400 is provided with a heater 454, such as a finned resistive heater which serves to maintain the temperature within mixing device 415, more specifically the temperature surrounding the pressurized transfer means 428 and 442, the premixing chamber 424 and in-line mixer 426. The apparatus also comprises a temperature sensor 464, which serves to monitor the temperature within container 406 and adjust the heater 454 accordingly.

Figure 12:
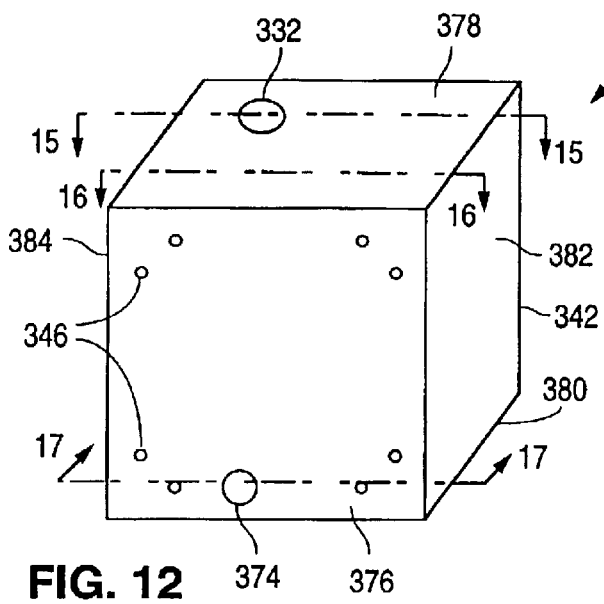
FIG. 12 illustrates another embodiment of a manifold.

FIG. 12 illustrates another embodiment of a manifold 423 useful in combination with the pump 425 of FIG. 10. This embodiment of the manifold will be described in relation to the transfer of the lipid phase. However, a similar configuration can be used for manifold 417 and pump 419, as pertains to the transfer of the aqueous phase. Similar to the pump, the manifold is provided with four inlets and four outlets. In the pump/manifold embodiment of FIG. 4, there are transfer means connecting the pump inlets/manifold outlets and pump outlets/manifold inlets. In the embodiment of FIG. 9, the various inlets and outlets are positioned on adjacent faces of the pump and manifold such that each pump outlet means communicates directly with a manifold inlet means, and each pump inlet means communicates directly with a manifold outlet means. In addition, the manifold has an inlet orifice that communicates with the storage vessel and an outlet orifice that communicates with the pre-mixing system, as described in detail below.

As with the pump in FIG. 5, the near "pulse-less" action is the pump is achieved by use of the four pump inlet means, each of which is 90° out of phase with the preceding inlet means and the successive inlet means. For example, referring to pump 425 shown in FIG. 13, there are four inlet means shown, 350, 352, 354 and 356. The operation curve of inlet means 352, for example, is out of phase by 90° from the operation curve of inlet means 352 and 356, and so forth. In operation then, these curves cancel each other out to provide for continuous, near "pulse-less" flow of the component from the vessel, to the manifold 423 to the pump 425, back to the manifold 423, then on to the pre-mixing chamber 424.

Figure 13:
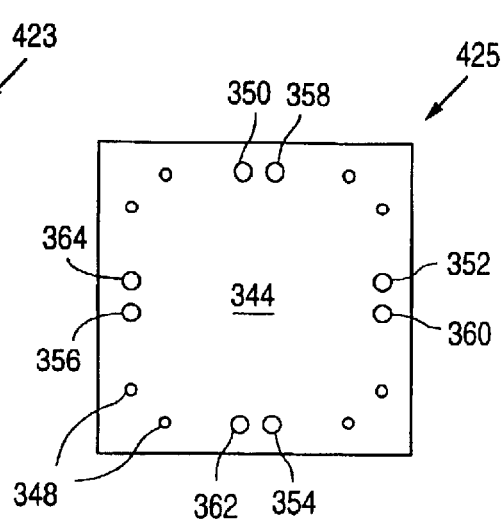
FIG. 13 illustrates the rear view of the manifold of FIG. 12.
Figure 14:
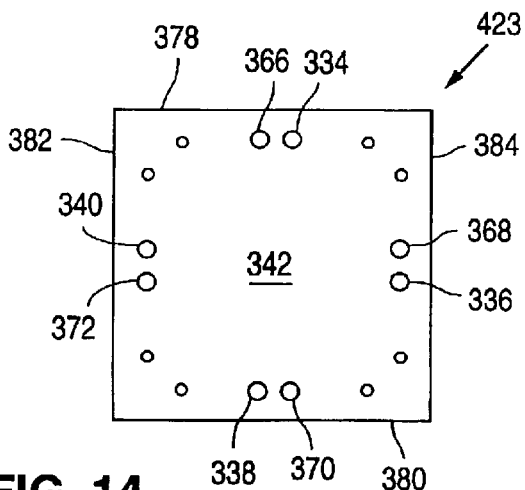
FIG. 14 illustrates the front view of a precise metering pump that engages the manifold of FIG. 12.

Referring now to FIG. 12, the lipid phase is transferred from its storage vessel 404 to the manifold 423 via pressurized transfer means 418 and manifold inlet orifice 332. The lipid phase is then transferred to the pump 425 by manifold outlet means 334, 336, 338 and 340, all of which are located on back face 342 of the manifold. FIG. 14 illustrates the back 342 of the manifold 423, which has the same configuration as the front face 344 of the precise metering pump 425, as shown in FIG. 13. The manifold and pump fit tightly together by means of an O-ring and a plurality of fastening means, which can be bolts for example. The bolts fit through a plurality of bored holes 346 that extend through the manifold 423 and match up with a plurality of bored holes 348 located on the face of the pump 425. The pump is fitted with four inlet means, 350, 352, 354 and 356 that communicate with manifold outlet means 334, 336, 338 and 340. As with the embodiment of FIG. 4, the pump has four positive pressure, positive displacement pumping chambers or cylinders, not shown. Pump inlet 350 and outlet 358 communicate with one cylinder, inlet 352 and outlet 360 communicate with another cylinder, and so forth.

The lipid phase then exits the pump through pump outlet means 358, 360, 362 and 364, which communicate with manifold inlet means 366, 368, 370 and 372. The lipid phase subsequently exits the manifold through manifold outlet orifice 374 located on the front face 376 of the manifold. Manifold outlet orifice 374 communicates with pressurized transfer means 442.

The manifold 423 is manufactured as a solid block of metal such as stainless steel or a suitable alloy such as the nickel alloy Hastelloy™. This manifold is configured as a square or rectangular box and, as shown in FIG. 12, has six sides or faces, which are identified as the front face 376, the back face 342, the top face 378, the bottom face 380, a first side face 382 and a second side face 384. The manifold is also configured to have two lateral planes, each of which marks the location of a set of independent flow channels. The two planes are best illustrated by reference to FIGS. 15 and 16, which are cross-sectional views of the manifold of FIG. 12, taken along lines 15—15 and 16—16, respectively.

Figure 15:
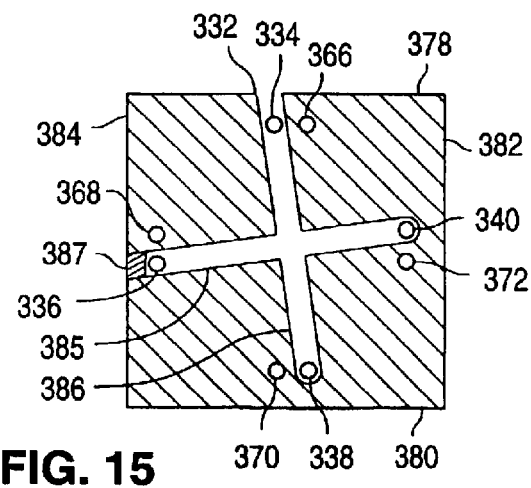
FIG. 15 is a cross-sectional view of a manifold, taken along line 15—15 of FIG. 12.

FIG. 15 illustrates a first lateral plane. A first and second set of transverse flow channels, 385 and 386 are positioned so as to intersect to form an "X". The first flow channel 385 is formed by boring an angled hole from side face 384 to a point some distance before side face 382 such that the channel 385 does not go through the entire manifold. The end of channel 385 is then plugged with plug 387, which prevents flow out of the manifold and can be made of threaded Teflon®, rubber, plastic and any other suitable materials that can be configured to fit securely in the channel. The second flow channel 386 is formed by boring an angled hole from the top face 378 to a point some distance before bottom face 380 such that the channel 386 does not go through the entire manifold. The end of channel 386 is left open to form manifold inlet orifice 332.

Figure 16:
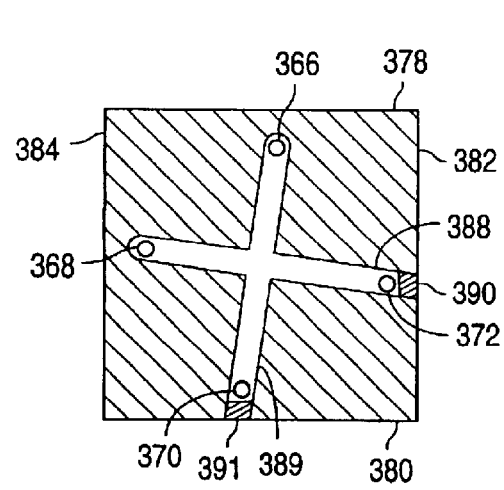
FIG. 16 is a cross-sectional view of a manifold, taken along line 16—16 of FIG. 12.

Referring now to FIG. 16, the second lateral plane is illustrated. A first and second set of transverse flow channels, 388 and 389 are positioned so as to intersect to form an "X". The first flow channel 388 is formed by boring an angled hole from side face 382 to a point some distance before side face 384 such that the channel 388 does not go through the entire manifold. The end of channel 388 is then plugged with plug 390. The second flow channel 389 is formed by boring an angled hole from the bottom face 380 to a point some distance before top face 378 such that the channel 389 does not go through the entire manifold. The end of channel 389 is then plugged with plug 391. It is important to understand that the flow channels in one lateral plane are independent from and do not communicate with the flow channels in the other lateral plane, i.e., there is no fluid flow between the channels 385, 386 in FIG. 15 and channels 388, 389 in FIG. 16.

Figure 17:
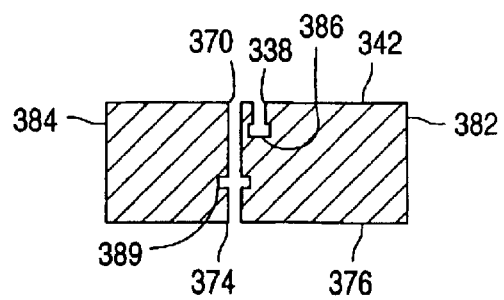
FIG. 17 is a cross-sectional view of a manifold, taken along line 17—17 of FIG. 12.

After the flow channels are bored into each lateral plane, a plurality of manifold inlet and outlet means are bored into the manifold to a pre-specified depth. Manifold inlet means 366, 368, 370 and 372 are drilled in the back face 342 to a depth sufficient to meet with and communicate with flow channels 388 and 389 in the lateral plane shown in FIG. 16. FIG. 17, which is a cross-sectional view of the manifold taken along line 17—17 in FIG. 12, illustrates this even further. It can be seen that manifold inlet means 370 is bored at a depth to meet with flow channel 389. Manifold outlet means 334, 336, 338 and 340 are drilled in the back face 342 to a depth sufficient to meet with and communicate with flow channels 385 and 386 in the lateral plane shown in FIG. 15. FIG. 17, which is a cross-sectional view of the manifold taken along line 17—17 in FIG. 12, illustrates this even further. It can be seen that manifold inlet means 338 is bored at a depth to meet with flow channel 386. After the manifold inlet and outlet means are bored, the manifold outlet orifice 374 is bored in the face 376 to a depth sufficient to meet with and communicate with flow channel 389, as shown in FIG. 17.

In operation, the lipid phase enters the manifold 423 though the manifold inlet orifice 332. It flows through flow channels 385 and 386, and then exits the flow channels by means of manifold outlet means 334, 336, 338 and 340, which communicate with pump inlet means 350, 352, 354 and 356, respectively. Fluid moves through pump inlet 350 in to one of the pump cylinders then exits via outlet means 358, and so forth with all four inlets and outlets of the pump, such that the lipid phase exits the pump 425 as a pulsed stream by means of pump outlet means 358, 360, 362 and 364, which communicate with manifold inlet means 366, 368, 370 and 372, respectively. The lipid phase then enters and flows through flow channels 388 and 389, and exits the manifold through the manifold outlet orifice 374.

By the configuration of the manifold and the near "pulse-less" action of the pump, which uses a plurality of inlet and outlet means, each of which are 90° out of phase, a pulsed input is delivered to the pre-mixing system as a virtually pulse-less flow of lipid phase or aqueous phase.

FIGS. 18–20 illustrate typical embodiments of a monitoring and process control system useful for the operation of the apparatus described herein, and are exemplified for the apparatus 400 of FIG. 10. FIGS. 18 and 19 illustrate control panels for the invention that are fitted with a plurality of connectors, indicator lights and controllers, which are connected by appropriate wiring (not shown) to the parts of the apparatus that they control, monitor or provide power to.

FIG. 18 illustrates a first control panel 456. Temperature sensor connector 458 is attached to the lipid phase resistance temperature device 410, while power connector 460 provides power to the lipid phase heating element 414. Data communication terminal 462 is attached to a computer 466, for example by means of a standard 9-pin serial port. Indicator light 468 indicates whether the heating elements 412 and 414 and heater 454 are on or off. Similarly, indicator light 470 indicates when the controllers (as described in FIG. 19) and precise metering systems 420 and 422 are on or off.

FIG. 19 illustrates a second control panel 472. Temperature sensor connector 474 is attached to the aqueous phase resistance temperature device 408, while power connector 476 provides power to the aqueous phase heating element 412. Power connector 478 is attached to a remote communication port (not shown) that requires an interface card or converter. The remote communication port serves as an interface between the controllers 480, 482 and 484, and the computer that is used to interactively monitor, control, and record the operation of the device and its components systems. Controllers 480, 482 and 484 serve to control heating element 414, heating element 412, and heater 454, respectively.

FIG. 20 is the bottom view of a power distribution module 486, which is fitted with a heat exhaust 488. The module has an on-off switch 490 and power fuse 492 for the heating elements 414, 412 and heater 454. The module also is fitted with an on-off switch 500 and power fuse 494 for the controllers 480, 482 and 484, and precise metering systems 420 and 422. In addition, there is a heater relay cooling fan 496 and main power input connector 498.

The instant invention also contemplates methods of producing lipid vesicles using a continuous in-line mixing system. In one embodiment of the invention, the method involves first preparing a lipid phase, optionally containing an active agent, and storing the lipid phase in a first storage means that is maintained at a set temperature, typically within the range of about 20 to 80° C. Similarly, an aqueous phase is prepared and stored in a second storage means that is maintained at a set temperature, typically also within the range of about 20 to 80° C. In one embodiment of the invention, the first and second storage means are continuously replenished with the lipid and aqueous phases, respectively.

The lipid and aqueous phases are then combined by means of a mixing device that has a first and a second metering system, a pre-mixer and a mixer. The mixer is typically maintained at a temperature within the range of about 20 to 80° C.

The lipid phase is transferred from the first storage means to the first metering system by a first pressurized transfer means and the aqueous phase is transferred from the second storage means to the second metering system by a second pressurized transfer means. The lipid phase is then transferred from the first metering system to a first inlet orifice in the pre-mixing system by a third pressurized transfer means. Similarly, the aqueous phase is transferred from the second metering system to a second inlet orifice in the pre-mixing system by a fourth pressurized transfer means. In operation of one embodiment of the invention, the lipid phase is transferred by the first and third pressurized transfer at a fluid flow rate of about 4 to 80 cm$^3$/sec, and the aqueous phase is transferred by the second and fourth pressurized transfer means at a fluid flow rate of about 10 to 100 cm$^3$/sec.

The lipid phase and aqueous phases are transferred to the pre-mixing system with a high velocity, which creates turbulent flow. Preferably, the lipid phase and aqueous phases are transferred to the pre-mixing system in a precise ratio. In another preferred embodiment, the lipid phase and aqueous phases are transferred to the pre-mixing system in a near pulse-less flow. The lipid and aqueous phases are then combined in the pre-mixing system by shear mixing under conditions to insure that the lipid phase becomes fully hydrated by the aqueous phase to form a pre-mixed formulation.

The pre-mixed formulation is then transferred from the outlet orifice of the pre-mixing system to the mixer by a fifth pressurized transfer means or other suitable connection or fitting. A mixed formulation, containing lipid vesicles, is formed in the mixer by causing the pre-mixed formulation to traverse a static mixer. The optical properties of the lipid vesicles are optionally measured. This can be accomplished by means of an optical transmission sensing device that uses a photoresistor or phototransistor, which provides a control signal to a controlling computer or other process control device, which in turn functions to control or adjust the temperatures of the first and second storage means, along with controlling the operation of the first and second metering systems.

In the final step, the mixed formulation is dispensed from the mixing chamber into a storage chamber, into a means for further modification of the properties of the lipid vesicles, or into a means of packaging the mixed formulation.

In another embodiment, the method includes a homogenization or sonication step after the dispensing step. This latter embodiment is useful for the production of unilamellar lipid vesicles. The method may also include the addition of a second lipid phase and/or a pre-mixed lipid phase-aqueous phase mixture.

In yet another preferred embodiment of the invention, each metering system in the method described above has a precise metering pump and a manifold. Each pump and manifold has a plurality of inlet and outlet means, where each pump inlet means communicates with a manifold outlet means and each pump outlet means communicates with a manifold inlet means. Each pump inlet means is 90° out of phase with the preceding inlet means and the successive inlet means. Along with a plurality of inlet and outlet means, the manifold also has a manifold outlet orifice and a manifold inlet orifice. In this embodiment, the method includes the steps of transferring the lipid phase to the inlet orifice of a first manifold by the first pressurized transfer means and simultaneously transferring the aqueous phase to the inlet orifice of a second manifold by the second pressurized transfer means; transferring the lipid phase from the plurality of outlet means of the first manifold to the plurality of inlet means of a first pump and simultaneously transferring the aqueous phase from the plurality of outlet means of the second manifold to the plurality of inlet means of the second pump; transferring the lipid phase from the plurality of outlet means of the first pump to the plurality of inlet means of the first manifold and transferring the aqueous phase from the plurality of outlet means of the second pump to the plurality of inlet means of the second manifold; and transferring the lipid phase from the outlet orifice of the first manifold by the third pressurized transfer means and simultaneously transferring the aqueous phase from the outlet of the second manifold by the fourth pressurized transfer means.

For purposes of illustrating the method of the invention, two component streams will be described, a lipid phase and an aqueous phase. However, as described above for the apparatus of the invention, it is understood that additional single or mixed phase components streams may be added as desired. In addition, a stream of liposomes may also be included. By combining a liposome phase stream with an aqueous phase stream and lipid phase stream, liposomes in the liposome stream can be further encapsulated using the method and apparatus of the invention. One of skill in the art will readily understand how such additional streams can be incorporated, for example by an the addition of another storage vessel, metering system, etc., such as is described above.

As noted above, the present invention also pertains to a method for the continuous production of a composition of matter, such as lipid vesicles, by in-line mixing. In one embodiment of the invention, the method comprises: (a) preparing a first phase, such as a lipid phase, and storing the lipid phase in a first storage means that is maintained at a set temperature; (b) preparing a second phase, such as an aqueous phase, and storing the aqueous phase in a second storage means that is maintained at a set temperature; (c) combining the lipid and aqueous phases by means of a mixing device having first and second metering systems, a pre-mixing system and a mixer, by: transferring the lipid phase from the first storage means to the first metering system by a first pressurized transfer means and transferring the aqueous phase from the second storage means to the second metering system by a second pressurized transfer means; transferring the lipid phase from the first metering system to a first inlet orifice in the pre-mixing system by a third pressurized transfer means and transferring the aqueous phase from the second metering system to a second inlet orifice in the pre-mixing system by a fourth pressurized transfer means; wherein the lipid phase and aqueous phases are transferred to the pre-mixing system with a high velocity creating turbulent flow; combining the lipid and aqueous phases in the pre-mixing system by shear mixing under conditions to insure that the lipid phase becomes fully hydrated by the aqueous phase to form a pre-mixed formulation; and transferring the pre-mixed formulation from an outlet orifice of the pre-mixing system to the mixer, such as by a fifth pressurized transfer means or other suitable connection or fitting; (d) forming a mixed formulation containing lipid vesicles, in the mixer by causing the pre-mixed formulation to traverse a static mixer; (e) optionally measuring the optical properties of the lipid vesicles; and (f) dispensing the mixed formulation from the mixing chamber into a storage chamber, into a means for further modification of the properties of the lipid vesicles, or into a means of packaging the mixed formulation.

This embodiment is further illustrated by the following discussion. First, the aqueous and lipid phases are prepared and heated to the proper temperatures. An exemplary aqueous phase may be sterile water, a physiological saline solution, a buffer solution, an aqueous carbohydrate solution, deuterated water, or other isotopic forms of $H_2O$, buffered solutions of organic acids and bases, and the like, or any combination thereof. In addition, the aqueous phase may also contain a water soluble organic solvent such as by way of illustration and not limitation, polyhydric alcohols including glycerin, propylene glycol, polypropylene glycol, triethylene glycol, polyethylene glycol, diethylene glycol monoethyl ether, etc.; alcohols such as benzyl alcohols, etc.; ethers; ketones; esters and glycerin esters such as monoacetin, diacetin, glycerophosphoric acid, etc.; and various aromatic and aliphatic hydrocarbons including fluorocarbons. Typically the aqueous phase will consist of about 75 to 99wt % sterile water, preferably about 85 to 98 wt %.

An exemplary lipid phase may consist of, by way of illustration and not limitation, phospholipids such as phosphatidyl chlolines, lysophosphatidyl chlolines, phosphatidyl serines, phosphatidyl ethanolamines, phosphatidyl inositols, cardiolipin, and sphingomyelin; natural phospholipids such as egg yolk lecithin, soybean lecithin, and soybean oil based phospholipids; glycolipids, dialkyl-type synthetic surfactants; polar lipids and neutral lipids; fatty acids; and the like. In addition, the lipid phase may also contain materials such as stearylamine, phosphatidic acid, dicetyl phosphate, tocopherol, cholesterol, lanolin extracts propylene glycol, polyethylene glycol, polypropylene glycol, glycol ethers, ethanol, and the like. Typically the lipid phase will consist of about 5 to 20 weight percent (wt %) of a phospholipid, preferably about 8 to 12 wt %. The lipid phase typically contains an active agent in the amount of about 0.01 to 35 wt %, more preferably about 2 to 25 wt %. However, it is understood that lipid vesicles can be manufactured without any active agent contained therein, if desired.

It may be desirable to prepare the aqueous phase in an amount in excess of that needed to produce the desired formulation. This excess allows for the stabilization of the temperatures of the manifolds, precise metering pumps, along with the pre-mixer and in-line mixer assembly.

Typically, one may produce the aqueous phase in an amount equal to 1 to 3, more typically 1.4 to 2 times the amount required for the formulation. On the other hand, the lipid phase is produced in an amount approximate to that amount needed to produce the desired formulation.

Once prepared, the lipid phase is placed in one storage means and the aqueous phase is placed in another storage means. These formulations are only provided to exemplify the methods of the invention and are not intended to be limiting in any manner. It is expected that the method and apparatus described herein will work with any liposomal formulation that is desired to be produced, with the same results as described herein.

This instant invention also relates to lipid vesicles produced by the method and apparatus described herein. Accordingly, the invention contemplates lipid vesicles, either multilamellar, oligolamellar or unilamellar, produced by the various apparatus embodiments described above. In a similar manner, the invention contemplates lipid vesicles, either multilamellar, oligolamellar or unilamellar, produced by the various method embodiments described above. Any of the aforementioned lipid vesicles can further comprise an active agent encapsulated in either the aqueous core of the lipid vesicles, within the lipid bilayer of the lipid vesicles, or both. Of particular interest are the active agents ivermectin and diclofenac.

As recognized by those skilled in the art, while certain materials and procedures may give better results, the use of particular materials and procedures are not critical to the invention and optimum conditions can readily be determined using routine testing. In addition, the invention also contemplates the inclusion of additional materials in the formulations to facilitate drug delivery, formulation stability, and so forth. For example, some liposome formulations may acquire a gel-like consistency upon cooling to room temperature in the absence of any adjuvants. Accordingly, conventional thickeners and gelling agents would be added to provide a preparation having the desired consistency for topical application. Additionally, a preservative or antioxidant often will be added to the preparation.

The amount of active agent to be included in the liposomal preparation is not, per se, critical and can vary within wide limits depending upon the intended application and the lipid used. The level of the active agent in the final liposomal formulation of the invention can vary within the full range employed by those skilled in the art, e.g., from about 0.01 to 99.99 wt % of the active agent based on the total formulation and about 0.01–99.99 wt % carrier, etc. More typically, the active agent will be present at a level of about 0.01–80 wt %. Preferably, the active agent may be included in an amount of between about 0.01 to 10 wt % of the liposomal preparation and more preferably may be included in an amount of about 0.01 to 7 wt %.

In employing the active agent-liposome formulation produced with this invention for pharmaceutical use, any pharmaceutically acceptable mode of administration can be used. For example, products can be made to suit any accepted systemic or local route of administration such as are well known in the art, for example, via parenteral, oral (particularly for infant formulations), intravenous, nasal, bronchial inhalation (i.e., aerosol formulation), transdermal or topical routes, in the form of solid, semi-solid or liquid or aerosol dosage forms, such as, for example, tablets, pills, capsules, powders, liquids, lotions, solutions, emulsion, injectables, suspensions, suppositories, aerosols or the like. The formulations produced by the invention can also be manufactured as sustained or controlled release dosage forms, including depot injections, osmotic pumps, pills, transdermal (including electrotransport) patches lotions, creams and the like, for the prolonged administration of the active agent at a predetermined rate, preferably in unit dosage forms suitable for single administration of precise dosages. The formulations will include a conventional pharmaceutically acceptable carrier or excipient and the active agent and, in addition, may include other medicinal agents, pharmaceutical agents, carriers, adjuvants, etc. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients and carriers also include starch, cellulose, talc, glucose, lactose, sucrose, mannitol, gelatin, povidone, malt, rice, flour, chalk, silica gel, magnesium stearate, sodium stearate, glycerol monostearate, magnesium carbonate, sodium chloride, sodium saccharine, croscarmellose sodium, dried skim milk, glycerol, glycols such as propylene glycol, polyethylene and polypropylene glycols and their derivatives, esters, salts and combinations of glycols and other fatty alcohols or acids, water, low molecular weight alcohols such as ethanol, propanol, and the like.

The formulations of the invention also preferably contains an antioxidant such as, by means of illustration and not limitation, tocopherol, more specifically Vitamin E ($\alpha$-tocopherol), tocopherol derivatives, butylated hydroxyanisole, and butylated hydroxytoluene. Other suitable pharmaceutical carriers and their formulations are described in "Remington's Pharmaceutical Sciences" by E. W. Martin.

If desired, the liposome formulation may also contain minor amounts of non-toxic auxiliary substances such as wetting or emulsifying agents, pH buffering agents and the like, such as for example, sodium acetate, sorbitan monolaurate, triethanolamine oleate, etc.

Another aspect of the invention pertains to an improved method of producing compositions of matter such as emulsions, ointments and creams using the methods and apparatus described herein. The method and apparatus described above for the production of lipid vesicles are readily modified by one of skill in the art to produce any of a variety of other compositions by modifying the starting components and the process parameters. Such compositions can also be formulated to include a payload.

Emulsions are two-phase systems in which one liquid is dispersed through another liquid in the form of small droplets. When oil is the dispersed phase and an aqueous phase is the continuous phase, the system is designated as an oil-in-water ("O/W") emulsion. Conversely, where water or an aqueous solution is the dispersed phase and oil or oleaginous material is the continuous phase, the system is designated as a water-in-oil ("W/O") emulsion. Accordingly, emulsions can readily be produced by using an aqueous phase, optionally containing a surfactant, and an oil phase, optionally containing various other ingredients and excipients as a second phase.

Ointments are semisolid preparations that are intended for external application to the skin or mucous membranes. They are generally recognized as oleaginous bases containing petrolatum. Such ointments can readily produced by the method and apparatus described herein using a viscous thixotropic phase as a first phase and a non-viscous oil phase as a second phase.

Creams are viscous liquid or semisolid emulsions, and can also be designated as O/W or W/O. These can be formulated, or example, by using an emulsion phase and an aqueous phase.

Each of the patent applications, patents, publications, and other published documents mentioned or referred to in this specification is herein incorporated by reference in its entirety, to the same extent as if each individual patent application, patent, publication, and other published document was specifically and individually indicated to be incorporated by reference. While the present invention has been described with reference to the specific embodiments thereof, it should be understood by those skilled in the art that various changes may be made and equivalents may be substituted without departing from the true spirit and scope of the invention and the appended claims. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for the continuous production of lipid vesicles by in-line mixing, said method comprising:

(a) preparing a lipid phase and storing the lipid phase in a first storage means that is maintained at a set temperature;

(b) preparing an aqueous phase and storing the aqueous phase in a second storage means that is maintained at a set temperature;

(c) combining the lipid and aqueous phases by means of a mixing device having first and second metering systems, a pre-mixing system and a mixer, by: transferring the lipid phase from the first storage means to the first metering system by a first pressurized transfer means and transferring the aqueous phase from the second storage means to the second metering system by a second pressurized transfer means; transferring the lipid phase from the first metering system to a first inlet orifice in the pre-mixing system by a third pressurized transfer means and transferring the aqueous phase from the second metering system to a second inlet orifice in the pre-mixing system by a fourth pressurized transfer means; wherein the lipid phase and aqueous phases are transferred to the pre-mixing system with a high velocity creating turbulent flow; combining the lipid and aqueous phases in the pre-mixing system by shear mixing under conditions to insure that the lipid phase becomes fully hydrated by the aqueous phase to form a pre-mixed formulation; and transferring the pre-mixed formulation from an outlet orifice of the pre-mixing system to the mixer;

(d) forming a mixed formulation containing lipid vesicles, in the mixer by causing the pre-mixed formulation to traverse the mixer;

(e) optionally measuring the optical properties of the lipid vesicles; and (f) dispensing the mixed formulation from the mixer into a storage chamber, into a means for further modification of the properties of the lipid vesicles, or into a means of packaging the mixed formulation; wherein each metering system comprises a precise metering pump and a manifold, where each pump and manifold have a plurality of inlet and outlet means, each pump inlet means communicates with a manifold outlet means and each pump outlet means communicates with a manifold inlet means, where each pump inlet means is 90° out of phase with the preceding pump inlet means and the successive pump inlet means, and the manifold further comprises a manifold outlet orifice and a manifold inlet orifice.

2. The method of claim 1 wherein said lipid vesicles are multilamellar.

3. The method of claim 1 which further comprises a homogenization or sonication step after the dispensing step.

4. The method of claim 3 wherein said lipid vesicles are unilamellar.

5. The method of claim 1 wherein the lipid phase comprises an active agent.

6. The method of claim 1 wherein said first storage means is maintained at a temperature within the range of about 20 to 80° C.

7. The method of claim 1 wherein said second storage means is maintained at a temperature within the range of about 20 to 80° C.

8. The method of claim 1 wherein the step of measuring optical properties is by means of an optical transmission sensing device using a photoresistor or phototransistor, which provides a control signal to a controlling computer or other process control device.

9. The method of claim 1 which further comprises the addition of a second lipid phase, a pre-mixed lipid phase-aqueous phase mixture or a pre-formed lipid vesicle phase.

10. The method of claim 1 wherein the first and second storage means are continuously replenished with the lipid and aqueous phases, respectively.

11. The method of claim 1 wherein the pressures are within the range of about 10 to 90 psia.

12. The method of claim 1 wherein the fluid flow rate of the lipid phase is about 3 to 200 $cm^3$/sec, and the fluid flow rate of the aqueous phase is about 5 to 300 $cm^3$/sec.

13. The method of claim 1 wherein mixer is maintained at a temperature within the range of about 20 to 80° C.

14. The method of claim 1; the method further comprising:

transferring the lipid phase to the inlet orifice of a first manifold by the first pressurized transfer means and simultaneously transferring the aqueous phase to the inlet orifice of a second manifold by the second pressurized transfer means;

transferring the lipid phase from the plurality of outlet means of the first manifold to the plurality of inlet means of a first pump and simultaneously transferring the aqueous phase from the plurality of outlet means of the second manifold to the plurality of inlet means of the second pump;

transferring the lipid phase from the plurality of outlet means of the first pump to the plurality of inlet means of the first manifold and transferring the aqueous phase from the plurality of outlet means of the second pump to the plurality of inlet means of the second manifold; and transferring the lipid phase from the outlet orifice of the first manifold by the third pressurized transfer means and simultaneously transferring the aqueous phase from the outlet of the second manifold by the fourth pressurized transfer means.

15. The method of claim 14 wherein the lipid phase and aqueous phases are transferred to the pre-mixer a precise ratio.

16. The method of claim 14 wherein the lipid phase and aqueous phases are transferred to the pre-mixer in a near pulse-less flow.

17. Lipid vesicles produced by the method of claim 1.

18. The lipid vesicles of claim 17 wherein said lipid vesicles are multilamellar or oligolamellar.

19. The lipid vesicles of claim 18 which further comprise an active agent encapsulated in the aqueous core of said vesicles, within the lipid bilayer of said vesicles, or encapsulated in the aqueous core and within the lipid bilayer of said vesicles.

20. The lipid vesicles of claim 19 wherein said active agent is selected from the group consisting of ivermectin and diclofenac.

21. Lipid vesicles produced by the method of claim 13.

22. The lipid vesicles of claim 21 wherein said lipid vesicles are unilamellar.

23. The lipid vesicles of claim 22 which further comprise an active agent encapsulated in the aqueous core of said vesicles, within the lipid bilayer of said vesicles, or encapsulated in the aqueous core and within the lipid bilayer of said vesicles.

24. The lipid vesicles of claim 23 wherein said active agent is selected from the group consisting of ivermectin and diclofenac.

* * * * *